United States Patent
Aradottir et al.

(10) Patent No.: US 11,631,486 B2
(45) Date of Patent: Apr. 18, 2023

(54) SYSTEMS AND METHODS FOR OPTIMIZATION OF BOLUS TIMING RELATIVE TO MEAL EVENTS

(71) Applicant: Novo Nordisk A/S, Bagsvaerd (DK)

(72) Inventors: Tinna Bjoerk Aradottir, Copenhagen (DK); Henrik Bengtsson, Taastrup (DK); Pete Brockmeier, Copenhagen (DK); Jonas Kildegaard Pedersen, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 1070 days.

(21) Appl. No.: 16/323,551

(22) PCT Filed: Aug. 14, 2017

(86) PCT No.: PCT/EP2017/070587
§ 371 (c)(1),
(2) Date: Feb. 6, 2019

(87) PCT Pub. No.: WO2018/033515
PCT Pub. Date: Feb. 22, 2018

(65) Prior Publication Data
US 2019/0198148 A1    Jun. 27, 2019

(30) Foreign Application Priority Data
Aug. 17, 2016    (EP) .................... 16184422

(51) Int. Cl.
*G16H 20/17*    (2018.01)
*G16H 50/20*    (2018.01)
(Continued)

(52) U.S. Cl.
CPC ............. *G16H 20/17* (2018.01); *A61K 38/28* (2013.01); *A61M 5/14244* (2013.01);
(Continued)

(58) Field of Classification Search
CPC ........ G16H 20/17; G16H 50/30; G16H 50/70; G16H 50/20; G16H 20/60; G16H 10/60;
(Continued)

(56) References Cited

U.S. PATENT DOCUMENTS 8,527,208 B2    9/2013    Prud'homme et al.
9,897,565 B1 *  2/2018    Booth ................ G01N 27/3271
(Continued)

FOREIGN PATENT DOCUMENTS

CN    101308528 A    11/2008
CN    104520862 A    4/2015

OTHER PUBLICATIONS

Anonymous: "Spritz-Ess-Abstand", DocCheck Flexikon, Jun. 2, 2013 (Jun. 2, 2013), XP055342678, Retrieved from the Internet: URL: http://web.archive.org/web/20130602171712/http://flexikon.doccheck.com/de/Spritz-Ess-Abstand, retrieved on Mar. 2, 2017.

*Primary Examiner* — Michael Tomaszewski
(74) *Attorney, Agent, or Firm* — Wesley Nicolas

(57) ABSTRACT

Systems and methods are provided for optimizing short acting insulin medicament dosage timing relative to a meal event for a subject. Glucose measurements of the subject over a time course and the timing of the measurements are obtained. Meal events in the time course and information regarding when dosages were injected into the subject relative to the meal events is obtained. Bins, each for a different time range for when a dosage is injected relative to a meal event, are constructed. Each bin is assigned glucose measurements in one or more periods within the time course in which the subject injected the dosage within the time range associated with the bin. A glycaemic risk measure is determined for each bin with the assigned measurements and
(Continued)

used to identify an optimal relative time range for the subject. This is communicated to a health care practitioner or to the subject.

16 Claims, 17 Drawing Sheets

(51) Int. Cl.
| | |
|---|---|
| *G16H 50/70* | (2018.01) |
| *G16H 50/30* | (2018.01) |
| *G16H 20/60* | (2018.01) |
| *A61K 38/28* | (2006.01) |
| *A61M 5/142* | (2006.01) |
| *G16H 10/60* | (2018.01) |
| *A61B 5/145* | (2006.01) |
| *A61M 5/172* | (2006.01) |

(52) U.S. Cl.
CPC ............. *G16H 20/60* (2018.01); *G16H 50/20* (2018.01); *G16H 50/30* (2018.01); *G16H 50/70* (2018.01); *A61B 5/14532* (2013.01); *A61M 5/1723* (2013.01); *A61M 2230/201* (2013.01); *G16H 10/60* (2018.01)

(58) Field of Classification Search
CPC . A61K 38/28; A61M 5/14244; A61M 5/1723; A61M 2230/201; A61B 5/14532
USPC .............................. 702/19, 2–3; 705/19, 2–3
See application file for complete search history.

(56) References Cited

U.S. PATENT DOCUMENTS

| | | | |
|---|---|---|---|
| 10,391,242 B2 | 8/2019 | Agrawal et al. | |
| 11,373,759 B2 * | 6/2022 | Van Orden | ............ G16H 50/70 |
| 2005/0272640 A1 | 12/2005 | Doyle et al. | |
| 2008/0234943 A1 | 9/2008 | Ray et al. | |
| 2009/0253973 A1 * | 10/2009 | Bashan | .................. G16H 10/00 |
| | | | 604/67 |
| 2010/0198520 A1 | 8/2010 | Breton et al. | |
| 2011/0015511 A1 * | 1/2011 | Bousamra | .............. G16H 80/00 |
| | | | 434/262 |
| 2011/0071765 A1 | 3/2011 | Yodfat et al. | |
| 2011/0282321 A1 | 11/2011 | Steil et al. | |
| 2013/0289883 A1 * | 10/2013 | Bashan | .............. A61B 5/14532 |
| | | | 702/19 |
| 2014/0066884 A1 | 3/2014 | Keenan et al. | |
| 2014/0094745 A1 * | 4/2014 | Bashan | .................. G16H 20/10 |
| | | | 702/19 |
| 2015/0025495 A1 * | 1/2015 | Peyser | .................... G16Z 99/00 |
| | | | 604/504 |

* cited by examiner (B)

──── 422

Segment the first data set into a plurality of bins using the second data set. Each respective bin 234 in the plurality of bins is associated with a relative time interval 236 in a plurality of relative time intervals. Each respective relative time interval in the plurality of relative time intervals defines a different time range for when a short acting insulin medicament dosage was injected by the subject relative to a meal event. Each respective bin is assigned glucose measurements in the plurality of glucose measurements that are associated with one or more periods within the time course in which the subject took the short acting insulin medicament dosage within the relative time interval associated with the respective bin.

──── 424

Determine a first glycaemic risk measure 238 for each respective bin in the plurality of bins using the autonomous glucose measurements assigned to the respective bin, thereby forming a plurality of first glycaemic risk measures.

──── 426

The first glycaemic risk measure is calculated for a respective bin as: (i) a percentage of the time the glucose level of the subject is above a first target range across the glucose measurements assigned to the respective bin, (ii) a percentage of the time the glucose level of the subject is below the first target range across the glucose measurements assigned to the respective bin, (iii) a percentage of the time the glucose level of the subject is outside the first target range in the glucose measurement assigned to the respective bin, (iv) a measure of spread of the glucose measurements assigned to the respective bin, (v) a minimum glucose level in the glucose measurements assigned to the respective bin, or (vi) a maximum glucose level in the glucose measurements assigned to the respective bin.

──── 428

The first glycaemic risk measure is calculated for a respective bin in the plurality of bins as: (i) a range of the glucose measurements assigned to the respective bin, (ii) an interquartile range of glucose measurements assigned to the respective bin, (iii) a variance of the glucose measurements assigned to the respective bin, (iv) an average squared difference of the glucose measurements assigned to the respective bin from the mean ($\mu$) of the glucose measurements assigned to the respective bin ($\sigma^2$) computed as:

$$\sigma^2 = \frac{\sum_i^P (m_i - \mu)^2}{P}$$

where $m_i$ is the $i^{th}$ glucose measurement assigned to the respective bin, and P is a number of glucose measurements assigned to the respective bin, or (v) a standard deviation of the glucose measurements assigned to the respective bin computed as $\sqrt{\sigma^2}$.

424(cont)
430

The time course comprises a plurality of epochs. Each epoch corresponds to a relative time interval in the plurality of relative time intervals. The second data set specifies the relative time interval in the plurality of relative time intervals for each epoch in the plurality of epochs. The method further comprises sharing the second data set with the subject prior to the time course to enable the subject to inject the short acting insulin medicament dosage at times specified by the second data set relative to respective meal events during the time course. The segmenting the first data set comprises assigning, for each respective epoch in the plurality of epochs, all glucose measurements in the respective epoch to the corresponding bin in the plurality of bins specified for the respective epoch by the second data set. The determining the first glycaemic risk measure of a respective bin in the plurality of bin collectively uses autonomous glucose measurements assigned to the respective bin.

432

Each epoch is one week or less, five days or less, three days or less, two days or less, one day or less, or 12 hours or less.

434

A third data set 302 is obtained from an insulin pen used by the subject to apply the prescribed insulin regimen. The third data set comprises a plurality of insulin medicament records over the time course. Each record 304 comprises (i) a respective insulin medicament injection event 306 representing an insulin medicament injection of the short acting insulin medicament dosage into the subject using the insulin pen, and (ii) a corresponding electronic timestamp 308 generated by the pen upon occurrence of the injection. The obtaining the second data set comprises temporally matching meal events to insulin medicament records thereby determining an actual time difference for when the short acting insulin medicament dosage was injected by the subject for each meal event relative to the meal event. The segmenting the first data set comprises associating, for each respective meal event, a bin in the plurality of bins with the respective meal event using the second data set. The associating matches (i) the actual time difference and (ii) a corresponding relative time interval in the plurality of relative time intervals, and assigning, for each respective meal event, autonomous glucose measurements in the plurality of autonomous glucose measurements that occur within a time window that ranges from a first predetermined period of time before the respective meal event to a second predetermined period of time after the respective meal event, to the associated bin. The segmenting associates more than one meal event to each bin. The determining the first glycaemic risk measure of a respective bin collectively uses the glucose measurements assigned to the bin.

The method further comprises obtaining a third data set from an insulin pen used by the subject to apply the prescribed insulin regimen. The third data set comprises a plurality of insulin medicament records over the time course. Each insulin medicament record in the plurality of medicament records comprises (i) a respective insulin medicament injection event representing an insulin medicament injection of the short acting insulin medicament dosage into the subject using the insulin pen, and (ii) a corresponding electronic timestamp that is automatically generated by the insulin pen upon occurrence of the respective insulin medicament injection event. The obtaining the second data set comprises temporally matching respective meal events in the plurality of meal events to respective insulin medicament records thereby determining an actual time difference for when the short acting insulin medicament dosage was injected by the subject for each respective meal event. The identifying the plurality of meal events further comprises applying a first characterization to each meal event in the plurality of meal events. The first characterization is one of insulin regimen adherent and insulin regimen nonadherent. A respective meal event is deemed insulin regimen adherent when one or more medicament records in the plurality of medicament records has a timestamp that is within a predetermined amount of time of the respective meal event. A respective meal event is deemed insulin regimen nonadherent when no medicament record in the plurality of medicament records has a timestamp that is within the predetermined amount of time of the respective meal event. The segmenting the first data set comprises: determining, for each respective meal event in the plurality of meal events that is deemed insulin regimen adherent, which bin in the plurality of bins is associated with the respective meal event using the second data set by a procedure. The procedure comprises matching when a short acting insulin medicament dosage was injected by the subject relative to the respective meal event to a corresponding relative time interval in the plurality of relative time intervals, and assigning, for each respective meal event in the plurality of meal events, autonomous glucose measurements in the plurality of autonomous glucose measurements that occur within a time window that ranges from a first predetermined period of time before the respective meal event to a second predetermined period of time after the respective meal event, to the associated bin. The segmenting associates more than one meal event from the plurality of meal events to each bin in the plurality of bins. The determining the first glycaemic risk measure of a respective bin in the plurality of bins collectively uses autonomous glucose measurements assigned to the respective bin.

SYSTEMS AND METHODS FOR OPTIMIZATION OF BOLUS TIMING RELATIVE TO MEAL EVENTS

CROSS-REFERENCE TO RELATED APPLICATIONS

This application is a 35 U.S.C. § 371 National Stage application of International Application PCT/EP2017/070587 (published as WO 2018/033515), filed Aug. 14, 2017, which claims priority to European Patent Application 16184422.0, filed Aug. 17, 2016, the contents of all above-named applications are incorporated herein by reference.

TECHNICAL FIELD

The present disclosure relates generally to systems and methods for assisting subjects and health care practitioners in managing insulin treatment to diabetes, in which the timing of when to take a bolus injection using, for instance an insulin pen, relative to a meal event is optimized in order to minimize glycaemic risk to the subject.

BACKGROUND

Type 2 diabetes mellitus is characterized by progressive disruption of normal physiologic insulin secretion. In healthy individuals, basal insulin secretion by pancreatic β cells occurs continuously to maintain steady glucose levels for extended periods between meals. Also in healthy individuals, there is prandial secretion in which insulin is rapidly released in an initial first-phase spike in response to a meal, followed by prolonged insulin secretion that returns to basal levels after 2-3 hours.

Insulin is a hormone that binds to insulin receptors to lower blood glucose by facilitating cellular uptake of glucose, amino acids, and fatty acids into skeletal muscle and fat and by inhibiting the output of glucose from the liver. In normal healthy individuals, physiologic basal and prandial insulin secretions maintain euglycemia, which affects fasting plasma glucose and postprandial plasma glucose concentrations. Basal and prandial insulin secretion is impaired in Type 2 diabetes and early post-meal response is absent. To address these adverse events, subjects with Type 2 diabetes are provided with insulin medicament treatment regimens. Subjects with Type 1 diabetes are also provided with insulin medicament treatment regimens. The goal of these insulin medicament treatment regimens is to maintain a desired fasting blood glucose target level that will minimize estimated risk of hypo- and hyper-glycaemia.

Traditional insulin medicament delivery systems have included the use of pump systems that provide a frequent recurrent dosage of insulin medicament. More recently, additional types of delivery systems have been developed, such as insulin pens, which can be used to self-administer insulin medicament treatment regimens in the form of less frequent insulin medicament injections. A common approach to Type 1 and Type 2 diabetes using such delivery systems is to inject a single short acting insulin medicament (bolus) dosage in a prescribed insulin regimen for the subject in response to or in anticipation of a meal event. In such approaches, the subject injects the short acting insulin medicament dosage shortly before or after one or more meals each day to lower glucose levels resulting from such meals.

However, a problem arises in determining precisely when, relative to a meal, the short acting insulin medicament dosage should be injected. This problem is subject specific. That is, the optimal time relative to the meal in which to inject the short acting dosage varies from subject to subject, and depends on a number of subject specific factors such as insulin sensitivity, insulin action rate, insulin clearance rate, meal absorption rates, distribution volume, body weight, recent physical exertion of the subject to name a few such factors. As such, failure to inject the short acting (bolus) dosage at the optimal time can result in undesirable changes in glucose levels that may lead to hypo- and/or hyper-glycaemic events.

United States Patent Publication No. 20050272640 entitled "Method and Apparatus for Glucose Control and Insulin Dosing" to the University of California discloses methods for optimizing controller gains for an insulin pump in the context of a method for deriving the optimal dosage and timing of bolus insulin administration. However, the publication does not offer satisfactory teachings on determining and communicating to a subject an optimal time in which to self-administer an insulin medicament treatment relative to a particular meal using, for instance, insulin pens.

United States Patent Publication No. 20110072765 entitled "Device and Method for Alleviating Postprandial Hyperglycemia" to Roche Diabetes Care discloses systems, devices and methods for alleviating postprandial hyperglycemia. A bolus selector is provided, adopted for selecting a total bolus dose of a drug corresponding to at least one of the food intake time and the food intake type and a glucose concentration level of a user. In such embodiments, the bolus selector may further be adopted for dividing the total bolus dose into a first phase bolus dose scheduled for delivery using, for example, a first phase bolus delivery rate at a first phase bolus delivery time, and a second phase bolus dose, for example, scheduled for delivery using a second phase bolus delivery rate at a second phase bolus delivery time. However, like the 20050272640 publication, the 20110072765 publication does not offer satisfactory teachings on determining and communicating to a subject an optimal time in which to self-administer an insulin medicament treatment relative to a particular meal using, for instance, insulin pens.

United States Patent Publication No. 20110282321 entitled "Model predictive method and system for controlling and supervising insulin infusion" to Medtronic Minimed discloses methods and systems that apply model predictive strategies to the operation and monitoring of diabetes-management systems. Embodiments of the invention are directed to a system and method for using model predictive bolus estimation for optimizing delivery of insulin into the body to cover a meal of certain carbohydrate amount and type. Using this information and the current glucose and insulin state, an apriori glucose profile is predicted for a user defined insulin bolus based on the model. If the glucose profile is acceptable, the user can confirm the insulin bolus, which would then be delivered by the pump. If the predicted profile is unacceptable, the user can modify the bolus amount or type until an acceptable predicted glucose profile is obtained. Alternatively, the system can derive and suggest an insulin delivery strategy that would yield a predicted postprandial glucose profile according to predefined guidelines. In a further embodiment in connection with a diabetes-management system having a glucose sensor and an insulin pump, a supervisory model is used to predict the dynamical state of the system, namely, the current estimate of glucose concentration given a history of meals and past insulin delivery profile. At each point in time, the state estimate of glucose concentration is compared with the measured sensor glucose value. If the difference between the measured glucose and estimated glucose exceeds a pre-determined error value, the system can alert the user that the discrepancy may be attributed to a failing, or failed, glucose sensor or insulin catheter. Again the 20110282324 publication does not offer satisfactory teachings on determining and communicating to a subject an optimal time in which to self-administer an insulin medicament treatment relative to a particular meal using, for instance, insulin pens.

Given the above background, what is needed in the art are systems and methods for providing personalized guidance on the timing of when to take a bolus injection relative to meal events in order to minimize glycaemic risk.

SUMMARY

The present disclosure addresses the need in the art for systems and methods for providing improved insulin medicament prescription advice. In the present disclosure, short acting insulin medicament dosage timing relative to a meal event for a subject is optimized. Glucose measurements of the subject over a time course and the timing of the measurements are obtained. Meal events in the time course and information regarding when short acting dosages were injected into the subject relative to the meal events is obtained. Bins, each for a different time range for when a short acting dosage is injected relative to a meal event, are constructed. Each bin is assigned glucose measurements in one or more periods within the time course in which the subject injected the short acting dosage within the time range associated with the bin. A glycaemic risk measure is determined for each bin with the assigned measurements and used to identify an optimal relative time range for the subject. This is communicated to a health care practitioner or to the subject.

As such, one aspect of the present disclosure provides a device for optimizing a timing of a short acting insulin medicament dosage in a prescribed insulin regimen for a subject. The device comprises one or more processors and a memory. The memory comprises instructions that, when executed by the one or more processors, perform a method. In the method, a first data set is obtained. The first data set comprises a plurality of autonomous glucose measurements of the subject taken over a time course and, for each respective glucose measurement in the plurality of glucose measurements, a corresponding timestamp representing when in the time course the respective glucose measurement was made. In the method, a plurality of meal events that occurred during the time course is identified. Further, in the method, a second data set is obtained that specifies, for each respective meal event in the plurality of meal events, when a short acting insulin medicament dosage was injected by the subject relative to the respective meal event.

The first data set is segmented into a plurality of segments, wherein each segment comprises glucose measurements that are associated with a period related to a meal event of the plurality of meal events. The period may therefore include the occurrence of the meal event and the medicament injection. The plurality of segments of the first data set are binned into a plurality of bins using the second data set, wherein each segment, associated with a respective meal event, is binned by determining when the short acting insulin medicament dosage was injected by the subject relative to the occurrence of the respective meal event, wherein each respective bin in the plurality of bins is associated with a relative time interval in a plurality of relative time intervals. Each respective relative time interval in the plurality of relative time intervals defines a different time range for when a short acting insulin medicament dosage was injected by the subject relative to a meal event, and thereby each respective bin is assigned glucose measurements in the plurality of glucose measurements that are associated with one or more periods within the time course that are related to a meal event, in which the subject took the short acting insulin medicament dosage within the relative time interval associated with the respective bin, i.e., each respective bin is assigned one or more segments that are associated with a period within the time course that are related to a meal event, in which the subject took the short acting insulin medicament dosage within the relative time interval associated with the respective bin.

The occurrence of each of the plurality of meal events can be specified using the first data set. The occurrence can e.g. be determined as the onset of ingestion identified as a portion of the glucose measurement showing a characteristic glucose profile, whereby the portion of glucose measurements can be used to specify the occurrence of the meal event. Further, in the method, a first glycaemic risk measure is determined for each respective bin in the plurality of bins using the autonomous glucose measurements assigned to the respective bin, thereby forming a plurality of first glycaemic risk measures. An optimal relative time interval for the subject is identified, from among the plurality of relative time intervals associated with the plurality of bins, for injecting the short acting insulin medicament dosage for a prospective meal event using the plurality of first glycaemic risk measures. This optimal relative time interval is communicated to a health care practitioner associated with the subject or directly to the subject.

In some embodiments, the first glycaemic risk measure is calculated for a respective bin in the plurality of bins as: (i) a percentage of the time the glucose level of the subject is above a first target range across the glucose measurements assigned to the respective bin, (ii) a percentage of the time the glucose level of the subject is below the first target range across the glucose measurements assigned to the respective bin, (iii) a percentage of the time the glucose level of the subject is outside the first target range in the glucose measurement assigned to the respective bin, (iv) a measure of spread of the glucose measurements assigned to the respective bin, (v) a minimum glucose level in the glucose measurements assigned to the respective bin, or (vi) a maximum glucose level in the glucose measurements assigned to the respective bin.

In some embodiments, the first glycaemic risk measure is calculated for a respective bin in the plurality of bins as (i) a range of the glucose measurements assigned to the respective bin, (ii) an interquartile range of glucose measurements assigned to the respective bin, (iii) a variance of the glucose measurements assigned to the respective bin, (iv) an average squared difference of the glucose measurements assigned to the respective bin from the mean ($\mu$) of the glucose measurements assigned to the respective bin ($\sigma^2$) computed as:

$$\sigma^2 = \frac{\sum_{i}^{P}(m_i - \mu)^2}{P}$$

where $m_i$ is the $i^{th}$ glucose measurement assigned to the respective bin, and P is a number of glucose measurements assigned to the respective bin, or (v) a standard deviation of the glucose measurements assigned to the respective bin computed as $\sqrt{\sigma^2}$.

In some embodiments, the identifying the plurality of meal events is performed using the plurality of autonomous glucose measurements and the corresponding timestamps in the first data set. In some such embodiments, the identifying the plurality of meal events is performed by computing: (i) a first model comprising a backward difference estimate of glucose rate of change using the plurality of autonomous glucose measurements, (ii) a second model comprising a backward difference estimate of glucose rate of change based on Kalman filtered estimates of glucose using the plurality of autonomous glucose measurements, (iii) a third model comprising a Kalman filtered estimate of glucose and Kalman filtered estimate of rate of change (ROC) of glucose based on the plurality of autonomous glucose measurements, or (iv) a fourth model comprising a Kalman filtered estimate of rate of change of ROC of glucose based on the plurality of autonomous glucose measurements. In some such embodiments, the first model, the second model, the third model and the fourth model are each computed using the plurality of autonomous glucose measurements and each respective meal event in the plurality of meal events is identified at an instance where at least three of the four models indicate a meal event.

In some embodiments, the identifying the plurality of meal events that occur during the time course further comprises receiving a plurality of feed-forward events, where each respective feed-forward event in the plurality of feed-forward events represents an instance where the subject has indicated they are having or are about to have a meal. In such embodiments, the plurality of meal events are verified against the plurality of feed-forward events by removing any respective meal event in the plurality of meal events that fails to temporally match a feed-forward event in the plurality of feed-forward events.

In alternative embodiments, the identifying the plurality of meal events that occur during the time course comprises receiving a plurality of feed-forward events, where each respective feed-forward event in the plurality of feed-forward events represents an instance where the subject has indicated they are having or are about to have a meal.

In some embodiments, the time course comprises a plurality of epochs. Each epoch corresponds to a relative time interval in the plurality of relative time intervals. The second data set specifies the relative time interval in the plurality of relative time intervals for each epoch in the plurality of epochs. In such embodiments, the method further comprises sharing the second data set with the subject prior to the time course to enable the subject to inject the short acting insulin medicament dosage at times specified by the second data set relative to respective meal events during the time course. Further, in such embodiments, the segmenting the first data set comprises assigning, for each respective epoch in the plurality of epochs, all glucose measurements in the respective epoch to the corresponding bin in the plurality of bins specified for the respective epoch by the first data set. Moreover, in such embodiments, the determining the first glycaemic risk measure of a respective bin in the plurality of bin collectively uses autonomous glucose measurements assigned to the respective bin. In some such embodiments, each epoch in the plurality of epochs is one week or less, five days or less, three days or less, two days or less, one day or less, or 12 hours or less.

In some embodiments, the method further comprises obtaining a third data set from an insulin pen used by the subject to apply the prescribed insulin regimen. The third data set comprises a plurality of insulin medicament records over the time course. Each insulin medicament record in the plurality of medicament records comprises (i) a respective insulin medicament injection event representing an insulin medicament injection of the short acting insulin medicament dosage into the subject using the insulin pen and (ii) a corresponding electronic timestamp that is automatically generated by the insulin pen upon occurrence of the respective insulin medicament injection event. In such embodiments, the obtaining the second data set comprises temporally matching respective meal events in the plurality of meal events to respective insulin medicament records thereby determining an actual time difference for when the short acting insulin medicament dosage was injected by the subject for each respective meal event relative to the respective meal event. Further, in such embodiments, the segmenting the first data set comprises: associating, for each respective meal event in the plurality of meal events, a bin in the plurality of bins with the respective meal event using the second data set. This associating matches (i) the actual time difference and (ii) a corresponding relative time interval in the plurality of relative time intervals, and assigned, for each respective meal event in the plurality of meal events, autonomous glucose measurements in the plurality of autonomous glucose measurements that occur within a time window that ranges from a first predetermined period of time before the respective meal event to a second predetermined period of time after the respective meal event, to the associated bin. Moreover, in such embodiments, the segmenting associates more than one meal event from the plurality of meal events to each bin in the plurality of bins. Further, in such embodiments, the determining the first glycaemic risk measure of a respective bin in the plurality of bins collectively uses the autonomous glucose measurements assigned to the respective bin.

In some embodiments a third data set is obtained from an insulin pen used by the subject to apply the prescribed insulin regimen. The third data set comprises a plurality of insulin medicament records over the time course, each insulin medicament record in the plurality of medicament records comprising: (i) a respective insulin medicament injection event representing an insulin medicament injection of the short acting insulin medicament dosage into the subject using the insulin pen, and (ii) a corresponding electronic timestamp that is automatically generated by the insulin pen upon occurrence of the respective insulin medicament injection event. In such embodiments, the obtaining the second data set comprises temporally matching respective meal events in the plurality of meal events to respective insulin medicament records thereby determining an actual time difference for when the short acting insulin medicament dosage was injected by the subject for each respective meal event, the identifying the plurality of meal events further comprises applying a first characterization to each meal event in the plurality of meal events, wherein the first characterization is one of insulin regimen adherent and insulin regimen nonadherent, where a respective meal event is deemed insulin regimen adherent when one or more medicament records in the plurality of medicament records has a timestamp that is within a predetermined amount of time of the respective meal event, and a respective meal event is deemed insulin regimen nonadherent when no medicament record in the plurality of medicament records has a timestamp that is within the predetermined amount of time of the respective meal event. In such embodiments, the segmenting the first data set comprises: determining, for each respective meal event in the plurality of meal events that is deemed insulin regimen adherent, which bin in the plurality of bins is associated with the respective meal event using the second data set by a procedure comprising: matching when a short acting insulin medicament dosage was injected by the subject relative to the respective meal event to a corresponding relative time interval in the plurality of relative time intervals, and assigning, for each respective meal event in the plurality of meal events, autonomous glucose measurements in the plurality of autonomous glucose measurements that occur within a time window that ranges from a first predetermined period of time before the respective meal event to a second predetermined period of time after the respective meal event, to the associated bin. Further, the segmenting associates more than one meal event from the plurality of meal events to each bin in the plurality of bins. In such embodiments, the determining the first glycaemic risk measure of a respective bin in the plurality of bins collectively uses the autonomous glucose measurements assigned to the respective bin.

In some embodiments, successive measurements in the plurality of glucose measurements are autonomously taken from the subject at an interval rate of 5 minutes or less, 3 minutes or less, or 1 minute or less.

In some embodiments, a respective second glycaemic risk measure is determined for each respective bin in the plurality of bins using the autonomous glucose measurements in the respective bin, thereby forming a plurality of second glycaemic risk measures. In such embodiments, the second respective glycaemic risk measure is other than the first glycaemic measure and is calculated for a respective bin in the plurality of bins as: (i) a percentage of the time the glucose level of the subject is above a first target range across the glucose measurements assigned to the respective bin, (ii) a percentage of the time the glucose level of the subject is below the first target range across the glucose measurements assigned to the respective bin, (iii) a percentage of the time the glucose level of the subject is outside the first target range in the glucose measurement assigned to the respective bin, (iv) a measure of spread of the glucose measurements assigned to the respective bin, (v) a minimum glucose level in the glucose measurements assigned to the respective bin, or (vi) a maximum glucose level in the glucose measurements assigned to the respective bin. In such embodiments, the identifying the optimal relative time interval for the subject, from among the plurality of relative time intervals associated with the plurality of bins, for injecting the short acting insulin medicament dosage for a prospective meal event uses the plurality of first glycaemic risk measures and the plurality of second glycaemic risk measures.

Another aspect of the present disclosure provides a method for optimizing a timing of a short acting insulin medicament dosage in a prescribed insulin regimen for a subject, the method comprising: at a computer comprising one or more processors and a memory:
  obtaining a first data set, the first data set comprising a plurality of autonomous glucose measurements of the subject taken over a time course and, for each respective glucose measurement in the plurality of glucose measurements, a corresponding timestamp representing when in the time course the respective glucose measurement was made;
  identifying a plurality of meal events in the first data set that occurred during the time course;
  obtaining a second data set that specifies, for each respective meal event in the plurality of meal events, when a short acting insulin medicament dosage was injected by the subject relative to an occurrence of the respective meal event;
  segmenting the first data set into a plurality of segments, wherein each segment comprises glucose measurements that are associated with a period related to a meal event of the plurality of meal events;
  binning the plurality of segments of the first data set into a plurality of bins using the second data set, wherein each segment, associated with a respective meal event, is binned by determining when the short acting insulin medicament dosage was injected by the subject relative to the occurrence of the respective meal event, wherein each respective bin in the plurality of bins is associated with a relative time interval in a plurality of relative time intervals,
  each respective relative time interval in the plurality of relative time intervals defines a different time range for when the short acting insulin medicament dosage was injected by the subject relative to the occurrence of the meal event, and
  each respective bin is assigned glucose measurements in the plurality of glucose measurements that are associated with one or more periods within the time course that are related to a meal event, in which the subject took the short acting insulin medicament dosage within the relative time interval associated with the respective bin;
  determining a first glycaemic risk measure for each respective bin in the plurality of bins using the autonomous glucose measurements assigned to the respective bin, thereby forming a plurality of first glycaemic risk measures;
  identifying an optimal relative time interval for the subject, from among the plurality of relative time intervals associated with the plurality of bins, for injecting the short acting insulin medicament dosage for a prospective meal event using the plurality of first glycaemic risk measures; and
  communicating the optimal relative time interval to a health care practitioner associated with the subject or directly to the subject.

In a further aspect is provided a computer program comprising instructions that, when executed by one or more processors, perform the method of:
  obtaining a first data set, the first data set comprising a plurality of autonomous glucose measurements of the subject taken over a time course and, for each respective glucose measurement in the plurality of glucose measurements, a corresponding timestamp representing when in the time course the respective glucose measurement was made;
  identifying a plurality of meal events in the first data set that occurred during the time course;
  obtaining a second data set that specifies, for each respective meal event in the plurality of meal events, when a short acting insulin medicament dosage was injected by the subject relative to an occurrence of the respective meal event;
  segmenting the first data set into a plurality of segments, wherein each segment comprises glucose measurements that are associated with a period related to a meal event of the plurality of meal events;
  binning the plurality of segments of the first data set into a plurality of bins using the second data set, wherein each segment, associated with a respective meal event, is binned by determining when the short acting insulin medicament dosage was injected by the subject relative to the occurrence of the respective meal event, wherein each respective bin in the plurality of bins is associated with a relative time interval in a plurality of relative time intervals, each respective relative time interval in the plurality of relative time intervals defines a different time range for when a short acting insulin medicament dosage was injected by the subject relative to a meal event, and each respective bin is assigned glucose measurements in the plurality of glucose measurements that are associated with one or more periods within the time course that are related to a meal event, in which the subject took the short acting insulin medicament dosage within the relative time interval associated with the respective bin;

determining a first glycaemic risk measure for each respective bin in the plurality of bins using the autonomous glucose measurements assigned to the respective bin, thereby forming a plurality of first glycaemic risk measures;

identifying an optimal relative time interval for the subject, from among the plurality of relative time intervals associated with the plurality of bins, for injecting the short acting insulin medicament dosage for a prospective meal event using the plurality of first glycaemic risk measures; and communicating the optimal relative time interval to a health care practitioner associated with the subject or directly to the subject.

In a further aspect is provided a computer-readable data carrier having stored thereon the computer program according to the above.

Another aspect of the present invention provides a device for optimizing a timing of a short acting insulin medicament dosage in a prescribed insulin regimen for a subject, wherein the device comprises one or more processors and a memory, the memory comprises instructions that, when executed by the one or more processors, perform a method of:

obtaining a first data set, the first data set comprising a plurality of autonomous glucose measurements of the subject taken over a time course and, for each respective glucose measurement in the plurality of glucose measurements, a corresponding timestamp representing when in the time course the respective glucose measurement was made;

identifying a plurality of meal events that occurred during the time course;

obtaining a second data set that specifies, for each respective meal event in the plurality of meal events, when a short acting insulin medicament dosage was injected by the subject relative to an occurrence of the respective meal event;

segmenting the first data set into a plurality of bins using the second data set, wherein each respective bin in the plurality of bins is associated with a relative time interval in a plurality of relative time intervals, each respective relative time interval in the plurality of relative time intervals defines a different time range for when a short acting insulin medicament dosage was injected by the subject relative to a meal event, and each respective bin is assigned glucose measurements in the plurality of glucose measurements that are associated with one or more periods within the time course in which the subject took the short acting insulin medicament dosage within the relative time interval associated with the respective bin;

determining a first glycaemic risk measure for each respective bin in the plurality of bins using the autonomous glucose measurements assigned to the respective bin, thereby forming a plurality of first glycaemic risk measures;

identifying an optimal relative time interval for the subject, from among the plurality of relative time intervals associated with the plurality of bins, for injecting the short acting insulin medicament dosage for a prospective meal event using the plurality of first glycaemic risk measures; and communicating the optimal relative time interval to a health care practitioner associated with the subject or directly to the subject.

BRIEF DESCRIPTION OF THE DRAWINGS

FIGS. 4A, 4B, 4C, 4D, 4E, and 4F collectively provide a flow chart of processes and features of a device for optimizing a timing of a short acting insulin medicament dosage in a prescribed insulin regimen for a subject, where optional elements of the flow chart are indicated by dashed boxes, in accordance with various embodiments of the present disclosure.

FIG. 7A is the average glucose concentration over three days, where insulin is injected at different times respectively to meal ingestion. No registered meal or injection data are available. FIG. 7B provides a glycaemic control evaluation compared to bolus injection timings. Panel 7A shows the time spent in hyperglycaemia, panel 7B shows the time spent in hypoglycaemia, and panel 7C shows daily variance, with the x-axis indicating minutes between the bolus injection event and the reference meal event. Positive minutes indicate injection times before meal ingestion, and negative minutes indicate injection times after meal ingestion.

Like reference numerals refer to corresponding parts throughout the several views of the drawings.

DETAILED DESCRIPTION

Figure 1:
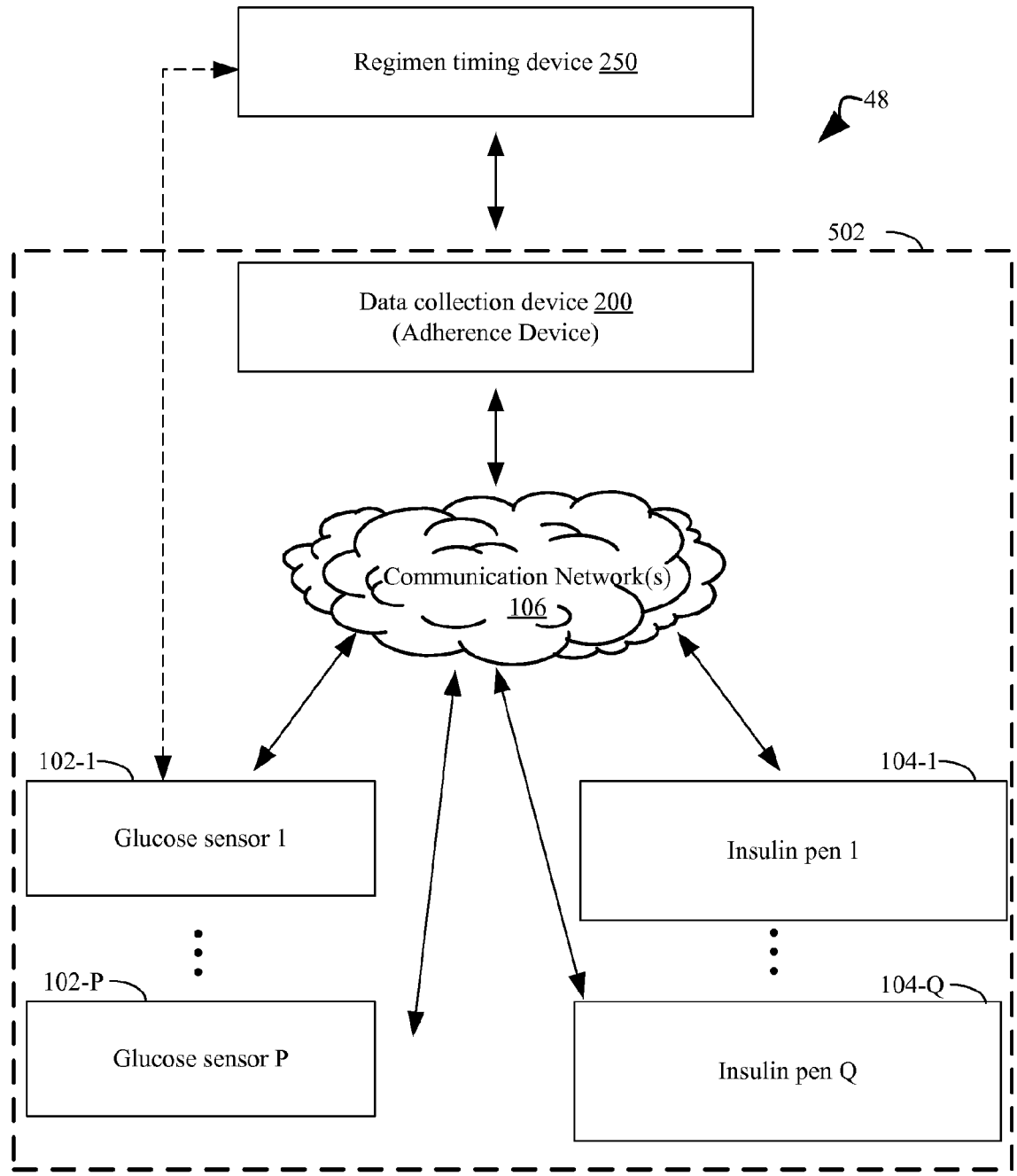
FIG. 1 illustrates an exemplary system topology that includes a regimen timing device for optimizing a timing of a short acting insulin medicament dosage in a prescribed insulin regimen for a subject, a data collection device for collecting patient data, one or more glucose sensors that measure glucose data from the subject, and one or more insulin pens that are used by the subject to inject insulin medicaments in accordance with the prescribed insulin regimen, where the above-identified components are interconnected, optionally through a communications network, in accordance with an embodiment of the present disclosure.
Figure 5:
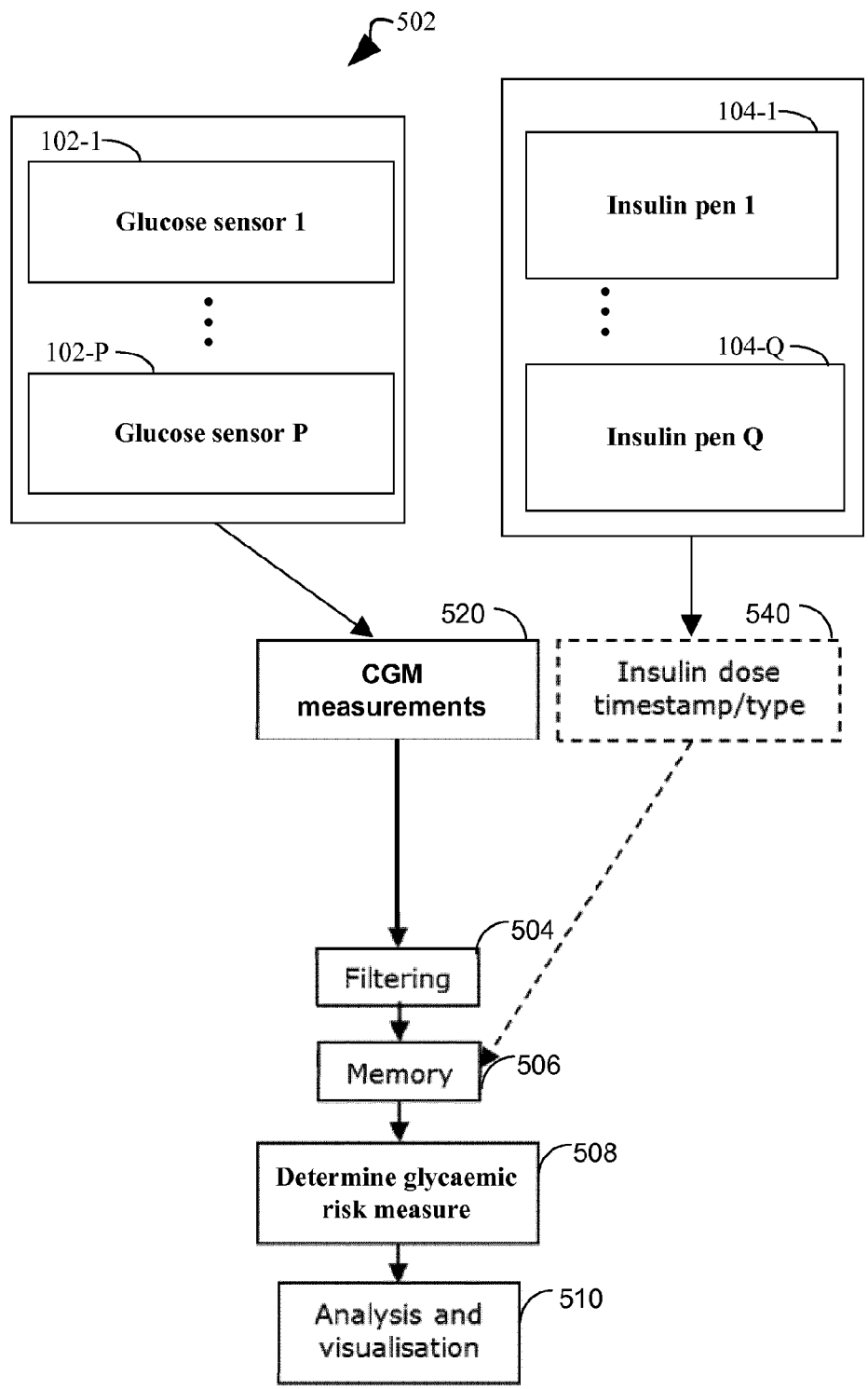
FIG. 5 illustrates an example integrated system of connected insulin pen(s), continuous glucose monitor(s), memory and a processor for optimizing a timing of a short acting insulin medicament dosage in a prescribed insulin regimen for a subject in accordance with an embodiment of the present disclosure.

The present disclosure relies upon the acquisition of a data set comprising a plurality of autonomous glucose measurements of a subject taken over a time course and, for each respective glucose measurement in the plurality of glucose measurements, a corresponding timestamp representing when in the time course the respective glucose measurement was made. FIG. 1 illustrates an example of an integrated system 502 for the acquisition of such data, and FIG. 5 provides more details of such a system 502. The integrated system 502 includes one or more connected insulin pens 104, one or more glucose monitors 102, memory 506, and a processor (not shown) for optimizing a timing of a short acting insulin medicament dosage in a prescribed insulin regimen for a subject. In some embodiments, a glucose monitor 102 is a continuous glucose monitor.

With the integrated system 502, autonomous timestamped glucose measurements of the subject are obtained 520. Also, in some embodiments, data from the one or more insulin pens 104 used to apply a prescribed insulin regimen to the subject is obtained 540 as a plurality of records. Each record comprises a timestamped event specifying an amount of injected insulin medicament that the subject received as part of the prescribed insulin medicament dosage regimen. The autonomous glucose measurements are filtered 504 and stored in non-transitory memory 506. The plurality of autonomous glucose measurements of the subject taken over a time course are used to determine the glycaemic risk measure of the subject 508. In this way, the glucose data is analyzed and visualized (e.g., to optimize a timing of a short acting insulin medicament dosage in a prescribed insulin regimen for a subject) in accordance with the methods of the present disclosure 510.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein. By the term insulin pen is meant an injection device suitable for applying discrete doses of insulin, where the injection device is adapted for logging and communicating dose related data.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 2:
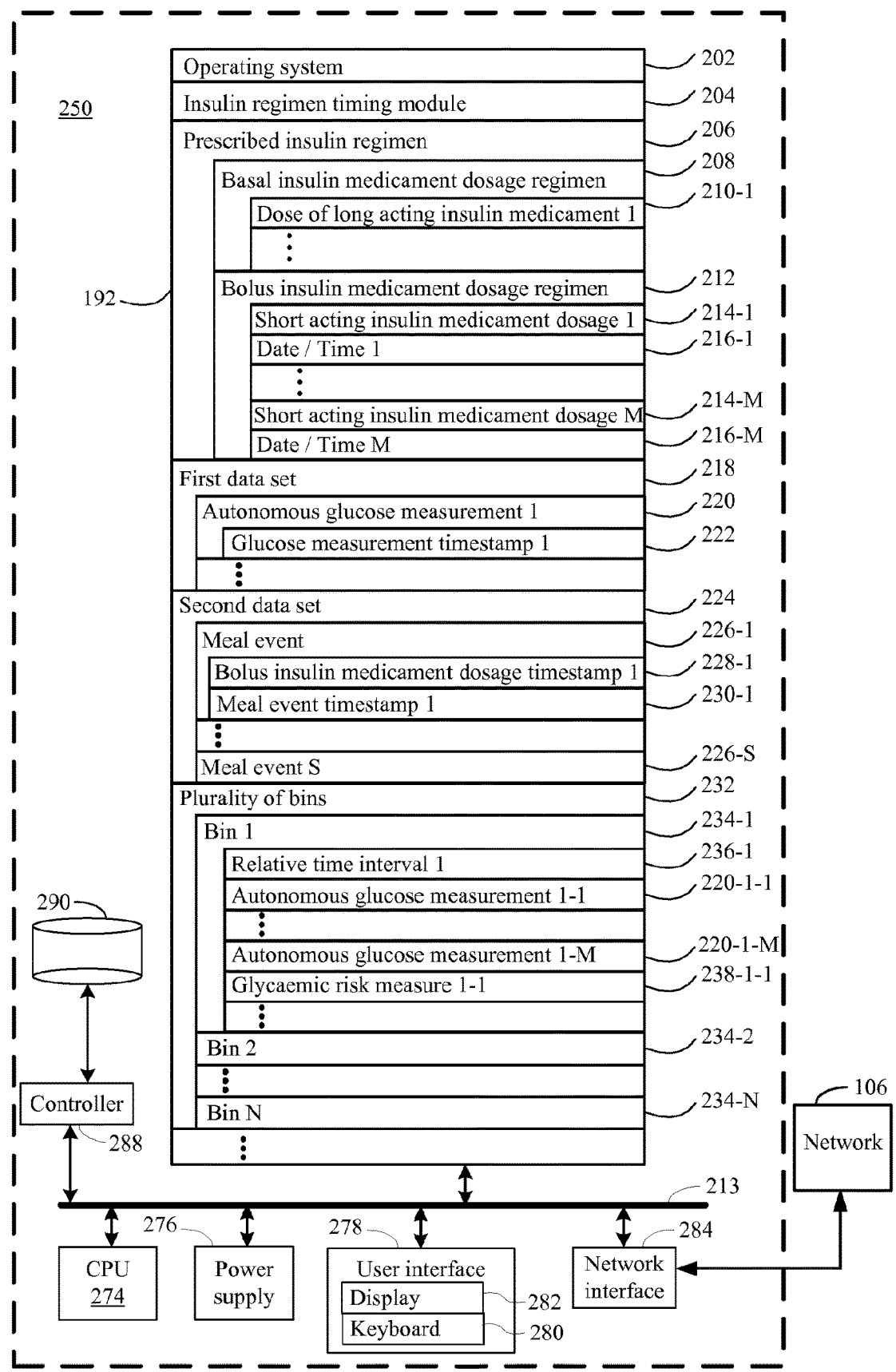
FIG. 2 illustrates a device for optimizing a timing of a short acting insulin medicament dosage in a prescribed insulin regimen for a subject in accordance with an embodiment of the present disclosure.
Figure 3:
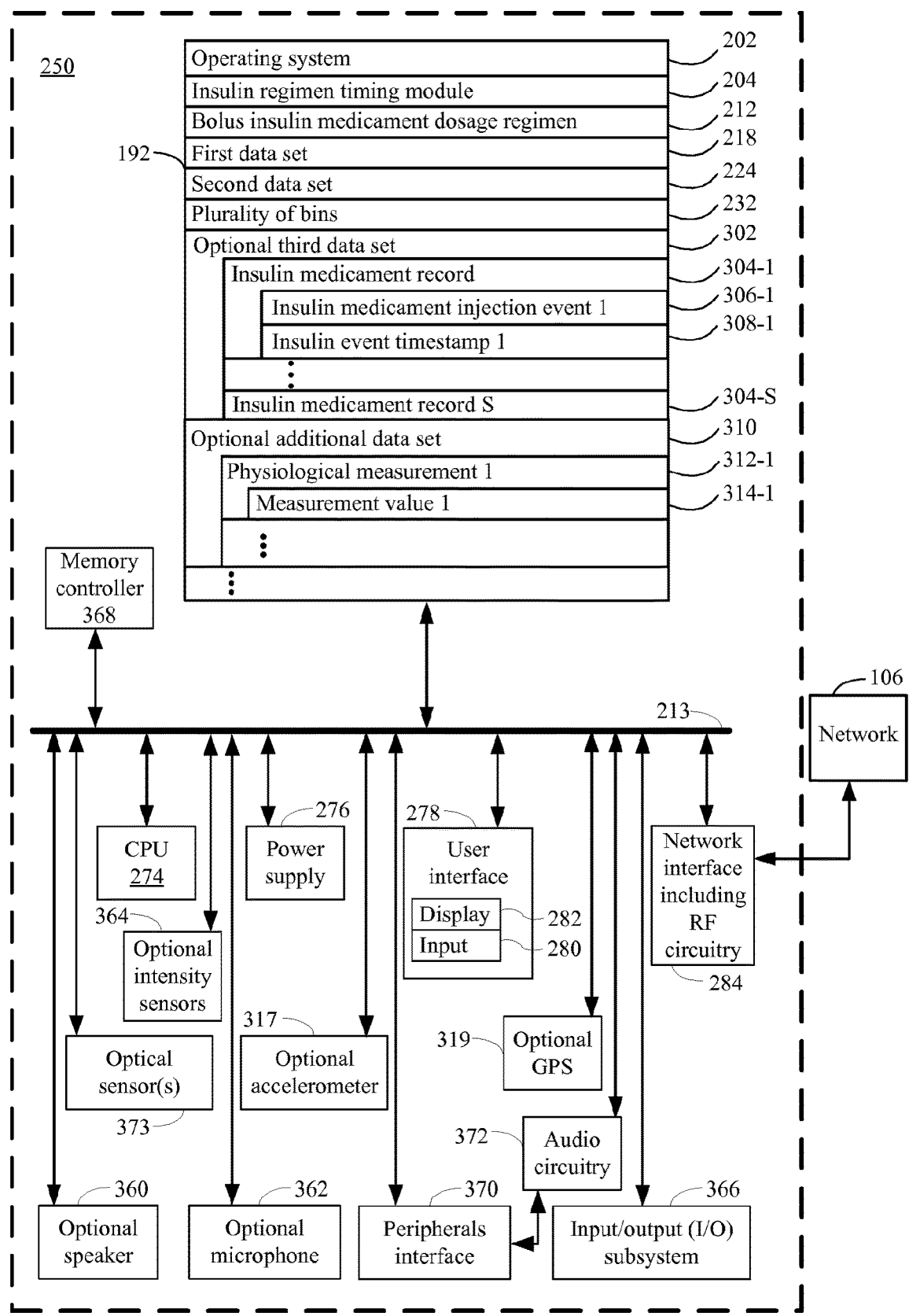
FIG. 3 illustrates a device for optimizing a timing of a short acting insulin medicament dosage in a prescribed insulin regimen for a subject in accordance with another embodiment of the present disclosure.

A detailed description of a system 48 for optimizing a timing of a short acting insulin medicament dosage in a prescribed insulin regimen for a subject in accordance with the present disclosure is described in conjunction with FIGS. 1 through 3. As such, FIGS. 1 through 3 collectively illustrate the topology of the system in accordance with the present disclosure. In the topology, there is a regimen timing device for optimizing a timing of a short acting insulin medicament dosage in a prescribed insulin regimen for a subject ("regimen timing device 250") (FIGS. 1, 2, and 3), a device for data collection ("data collection device 200"), one or more glucose sensors 102 associated with the subject (FIGS. 1 and 5), and one or more insulin pens 104 for injecting insulin medicaments into the subject (FIGS. 1 and 5). Throughout the present disclosure, the data collection device 200 and the regimen timing device 250 will be referenced as separate devices solely for purposes of clarity. That is, the disclosed functionality of the data collection device 200 and the disclosed functionality of the regimen timing device 250 are contained in separate devices as illustrated in FIG. 1. However, it will be appreciated that, in fact, in some embodiments, the disclosed functionality of the data collection device 200 and the disclosed functionality of the regimen timing device 250 are contained in a single device. In some embodiments, the disclosed functionality of the data collection device 200 and/or the disclosed functionality of the regimen timing device 250 are contained in a single device and this single device is a glucose monitor 102 or an insulin pen 104.

Referring to FIG. 1, the regimen timing device 250 optimizes a timing of a short acting insulin medicament dosage in a prescribed insulin regimen for a subject. To do this, the data collection device 200, which is in electrical communication with the regimen timing device 250, receives autonomous glucose measurements originating from one or more glucose sensors 102 attached to a subject on an ongoing basis. In some embodiments, the data collection device 200 also receives insulin medicament injection data from one or more insulin pens 104 used by the subject to inject insulin medicaments. In some embodiments, the data collection device 200 receives such data directly from the glucose sensor(s) 102 and insulin pens 104 used by the subject. For instance, in some embodiments the data collection device 200 receives this data wirelessly through radio-frequency signals. In some embodiments such signals are in accordance with an 802.11 (WiFi), Bluetooth, or ZigBee standard. In some embodiments, the data collection device 200 receives such data directly, analyzes the data, and passes the analyzed data to the regimen timing device 250. In some embodiments, a glucose sensor 102 and/or insulin pen 104 includes an RFID tag and communicates to the data collection device 200 and/or the regimen timing device 250 using RFID communication. In some embodiments, referring to FIG. 3, the data collection device 200 also obtains or receives physiological measurements 312 of the subject (e.g., from wearable physiological measurement devices, from measurement devices within the data collection device 200 such as a magnetometer or a thermostat, etc.).

In some embodiments, the data collection device 200 and/or the regimen timing device 250 is not proximate to the subject and/or does not have wireless capabilities or such wireless capabilities are not used for the purpose of acquiring autonomous glucose data, insulin medicament injection data, and/or physiological measurement data. In such embodiments, a communication network 106 may be used to communicate autonomous glucose measurements from the glucose sensor 102 to the data collection device 200 and/or the regimen timing device 250, insulin medicament injection data from the one or more insulin pens 104 to the data collection device 200 and/or the regimen timing device 250, and/or physiological measurement data from one or more physiological measurement devices (not shown) to the data collection device 200 and/or the regimen timing device 250.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

In some embodiments, there is a single glucose sensor 102 attached to the subject and the data collection device 200 and/or the regimen timing device 250 is part of the glucose sensor 102. That is, in some embodiments, the data collection device 200 and/or the regimen timing device 250 and the glucose sensor 102 are a single device.

In some embodiments, the data collection device 200 and/or the regimen timing device 250 is part of an insulin pen. That is, in some embodiments, the data collection device 200 and/or the regimen timing device 250 and an insulin pen 104 are a single device.

Of course, other topologies of the system 48 are possible. For instance, rather than relying on a communications network 106, the one or more glucose sensors 102 and the one or more insulin pens 104 may wirelessly transmit information directly to the data collection device 200 and/or regimen timing device 250. Further, the data collection device 200 and/or the regimen timing device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the regimen timing device 250 comprises one or more computers. For purposes of illustration in FIG. 2, the regimen timing device 250 is represented as a single computer that includes all of the functionality for optimizing a timing of a short acting insulin medicament dosage in a prescribed insulin regimen for a subject. However, the disclosure is not so limited. In some embodiments, the functionality for optimizing a timing of a short acting insulin medicament dosage in a prescribed insulin regimen for a subject is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary regimen timing device 250 for optimizing a timing of a short acting insulin medicament dosage in a prescribed insulin regimen for a subject comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the regimen timing device 250 but that can be electronically accessed by the regimen timing device 250 over an Internet, intranet, or other form of network or electronic cable (illustrated as element 106 in FIG. 2) using network interface 284.

In some embodiments, the memory 192 of the regimen timing device 250 for optimizing a timing of a short acting insulin medicament dosage in a prescribed insulin regimen for a subject stores:

- an operating system 202 that includes procedures for handling various basic system services;
- an insulin regimen timing module 204;
- a prescribed insulin regimen 206 for the subject, the prescribed insulin regimen comprising a short acting insulin medicament dosage regimen 212 with dosages 214 specified for certain dates or times 216, the prescribed insulin regimen further optionally comprising, in some embodiments, a basal insulin medicament dosage regimen 208 specifying dosages of long acting insulin medicament 210;
- a first data set 218, the first data set representing a time course and comprising a plurality of autonomous glucose measurements of the subject over the time course, and for each respective glucose measurement 220 in the plurality of glucose measurements, a glucose measurement timestamp 222 representing when the respective autonomous glucose measurement was made;
- a second data set 224 that comprises, for each respective meal event 226 in a plurality of meal events of the subject, a bolus insulin medicament dosage timestamp 228 and a corresponding meal event timestamp 230 for the respective meal event (or other information sufficient to ascertain when a bolus insulin medicament dosage was injected by the subject relative to an occurrence of the respective meal event);
- a plurality of bins 232, each respective bin 234 in the plurality of bins being associated with a relative time interval 236 in a plurality of relative time intervals, and each respective relative time interval in the plurality of relative time intervals defining a different time range for when a bolus insulin medicament dosage was injected by the subject relative to a meal event, and each respective bin being assigned glucose measurements in the plurality of glucose measurements that are associated with one or more periods within the time course in which the subject took the bolus insulin medicament dosage within the relative time interval associated with the respective bin, and each respective bin 234 further comprising one or more glycaemic risk measures 238 calculated using the autonomous glucose measurements in the respective bin.

In some embodiments, the insulin regimen timing module 204 is accessible within any browser (phone, tablet, laptop/desktop). In some embodiments the insulin regimen timing module 204 runs on native device frameworks, and is available for download onto the regimen timing device 250 running an operating system 202 such as Android or iOS.

In some implementations, one or more of the above identified data elements or modules of the regimen timing device 250 for optimizing a timing of a short acting insulin medicament dosage in a prescribed insulin regimen for a subject are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a regimen timing device 250 for optimizing a timing of a short acting insulin medicament dosage in a prescribed insulin regimen for a subject is a smart phone (e.g., an iPHONE), laptop, tablet computer, desktop computer, or other form of electronic device (e.g., a gaming console). In some embodiments, the regimen timing device 250 is not mobile. In some embodiments, the regimen timing device 250 is mobile.

FIG. 3 provides a further description of a specific embodiment of a regimen timing device 250 that can be used with the instant disclosure. The regimen timing device 250 illustrated in FIG. 3 has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the regimen timing device 250 (e.g., a touch-sensitive surface such as a touch-sensitive display system 282 of the regimen timing device 250), an optional input/output (I/O) subsystem 366, one or more optional optical sensors 373, one or more communication busses 213 for interconnecting the aforementioned components, and a power supply 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The regimen timing device 250 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the regimen timing device 250 and/or for determining an amount of physical exertion by the subject.

It should be appreciated that the regimen timing device 250 illustrated in FIG. 3 is only one example of a multifunction device that may be used for optimizing a timing of a short acting insulin medicament dosage in a prescribed insulin regimen for a subject, and that the regimen timing device 250 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 192 of the regimen timing device 250 illustrated in FIG. 3 optionally includes high-speed random access memory and optionally also includes non-volatile memory, such as one or more magnetic disk storage devices, flash memory devices, or other non-volatile solid-state memory devices. Access to memory 192 by other components of the regimen timing device 250, such as CPU(s) 274 is, optionally, controlled by the memory controller 368.

In some embodiments, the memory 192 of the regimen timing device 250 illustrated in FIG. 3 optionally includes a third data set 302 comprising a plurality of insulin medicament records over the time course. Each such insulin medicament record 304 in the plurality of medicament records comprises (i) a respective insulin medicament injection event 306 representing an insulin medicament injection of the short acting insulin medicament dosage 214 into the subject using the insulin pen, and (ii) a corresponding electronic timestamp 308 that is automatically generated by the insulin pen upon occurrence of the respective insulin medicament injection event.

In some embodiments, the memory 192 of the regimen timing device 250 illustrated in FIG. 3 optionally includes a data set 310 comprising a plurality of physiological measurements 312, and each such physiological measurement 312 includes a measurement value 314. In some embodiments, the physiological measurement 312 is body temperature of the subject. In some embodiments, the physiological measurement 312 is a measurement of activity of the subject. In some embodiments, these physiological measurements serve as an additional glycaemic risk measures. In some embodiments, these physiological measurements serve to verify or help to compute a glycaemic risk measure 238 in conjunction with the autonomous glucose measurements 220, meal events 226 and/or the insulin medicament records 304. In some embodiments, the optional accelerometer 317, optional GPS 319, and/or magnetometer (not shown) of the regimen timing device 250 or such components optionally within the one or more glucose monitors 102 and/or the one or more pens 104 is used to acquire such physiological measurements 312.

The peripherals interface 370 can be used to couple input and output peripherals of the device to CPU(s) 274 and memory 192. The one or more processors 274 run or execute various software programs and/or sets of instructions stored in memory 192, such as the insulin regimen timing module 204, to perform various functions for the regimen timing device 250 and to process data.

In some embodiments, the peripherals interface 370, CPU(s) 274, and memory controller 368 are, optionally, implemented on a single chip. In some other embodiments, they are implemented on separate chips.

RF (radio frequency) circuitry of network interface 284 receives and sends RF signals, also called electromagnetic signals. In some embodiments, the prescribed insulin regimen 206, the first data set 218, the second data set 224, the plurality of bins 232, the optional third data set 302, and/or the optional additional data set 310 is received using this RF circuitry from one or more devices such as a glucose sensor 102 associated with a subject, an insulin pen 104 associated with the subject and/or the data collection device 200. In some embodiments, the RF circuitry 108 converts electrical signals to/from electromagnetic signals and communicates with communications networks and other communications devices, glucose sensors 102, and insulin pens 104 and/or the data collection device 200 via the electromagnetic signals. The RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the regimen timing device 250. The audio circuitry 372 receives audio data from the peripherals interface 370, converts the audio data to electrical signals, and transmits the electrical signals to the speaker 360. The speaker 360 converts the electrical signals to human-audible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 192 and/or the RF circuitry 284 by the peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the regimen timing device 250 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the regimen timing device 250, opposite the display 282 on the front of the regimen timing device 250, so that the input 280 is enabled for use as a viewfinder for still and/or video image acquisition. In some embodiments, another optical sensor 373 is located on the front of the regimen timing device 250 so that the subject's image is obtained (e.g., to verify the health or condition of the subject, to determine the physical activity level of the subject, to help diagnose a subject's condition remotely, or to acquire visual physiological measurements 312 of the subject, etc.).

As illustrated in FIG. 3, a regimen timing device 250 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the regimen timing device 250 is a smart phone. In other embodiments, the regimen timing device 250 is not a smart phone but rather is a tablet computer, desktop computer, emergency vehicle computer, or other form or wired or wireless networked device. In some embodiments, the regimen timing device 250 has any or all of the circuitry, hardware components, and software components found in the regimen timing device 250 depicted in FIG. 2 or 3. In the interest of brevity and clarity, only a few of the possible components of the regimen timing device 250 are shown in order to better emphasize the additional software modules that are installed on the regimen timing device 250.

While the system 48 disclosed in FIG. 1 can work standalone, in some embodiments it can also be linked with electronic medical records to exchange information in any way.

Now that details of a system 48 for optimizing a timing of a short acting insulin medicament dosage in a prescribed insulin regimen for a subject have been disclosed, details regarding a flow chart of processes and features of the system, in accordance with an embodiment of the present disclosure, are disclosed with reference to FIGS. 4A through 4F. In some embodiments, such processes and features of the system are carried out by the insulin regimen timing module 204 illustrated in FIGS. 2 and 3.

Block 402. With reference to block 402 of FIG. 4A, the goal of insulin therapy in subjects with either type 1 diabetes mellitus or type 2 diabetes mellitus is to match as closely as possible normal physiologic insulin secretion to control fasting and postprandial plasma glucose. As illustrated in FIG. 2, a regimen timing device 250 comprises one or more processors 274 and a memory 192/290. The memory stores instructions that, when executed by the one or more processors, perform a method.

Blocks 404-406. In the method, a first data set 218 is obtained. The first data set 228 comprises a plurality of autonomous glucose measurements of the subject taken over a time course. In typical embodiments, the autonomous glucose measurements are from one or more glucose sensors 102. FIG. 2 illustrates. Each such glucose measurement 220 is timestamped with a glucose measurement timestamp 222 to represent when the respective measurement was made. Thus, in typical embodiments, the autonomous glucose measurements are measured without human intervention. That is, the subject does not manually make the autonomous glucose measurements. In alternative embodiments of the present disclosure, the subject or a health care practitioner manually takes glucose measurements and such manual glucose measurements are used as a substitute or a complement to the autonomous glucose measurements 220 in the first data set 218.

In embodiments where autonomous glucose measurements are used, devices such as the FREESTYLE LIBRE CGM by ABBOTT ("LIBRE") may serve as the glucose sensor 102 in order to make the plurality of autonomous glucose measurements of a subject. The LIBRE allows calibration-free glucose measurements with an on-skin coin-sized sensor, which can send up to eight hours of data to a reader device (e.g., the data collection device 200 and/or the regimen timing device 250) via near field communications, when brought close together. The LIBRE can be worn for fourteen days in all daily life activities. Referring to block 406, in some embodiments, the autonomous glucose measurements are autonomously taken from the subject at an interval rate of 5 minutes or less, 3 minutes or less, or 1 minute or less. In some embodiments, the autonomous glucose measurements are taken from the subject at an interval rate of 5 minutes or less, 3 minutes or less, or 1 minute or less, over a time period of a day or more, two days or more, a week or more, or two weeks or more. In some embodiments, the autonomous glucose measurements are autonomously taken (e.g., without human effort, without human intervention, etc.).

The regimen timing device 250 accesses and/or stores a prescribed insulin regimen 206 for the subject that is used to match as closely as possible normal physiologic insulin secretion to control fasting and postprandial plasma glucose. In the present disclosure, the prescribed insulin regimen 206 optionally comprises a short acting insulin medicament dosage regimen 208 that specifies at least one dose for a long acting insulin medicament dosage 210. In some embodiments, the short acting insulin medicament dosage regimen 208 specifies two or more doses, such as in instances where a daily basal dose has been split into two daily doses to optimize the treatment regimen. The prescribed insulin regimen 206 includes a bolus insulin medicament dosage regimen 212 which indicates at least one short acting insulin medicament dosage 214. For instance, in some embodiments, the bolus insulin medicament dosage regimen 212 specifies a first short acting insulin medicament dosage 214-1 for breakfast 216-1 and a second short acting insulin medicament dosage 214-2 for lunch 216-2. In some embodiments, the bolus insulin medicament dosage regimen 212 specifies a first short acting insulin medicament dosage 214-1 for breakfast 216-1, a second short acting insulin medicament dosage 214-2 for lunch 216-2, and a third short acting insulin medicament dosage 214-3 for dinner 216-3. In some embodiments, the bolus insulin medicament dosage regimen 212 specifies a first short acting insulin medicament dosage for a prospective meal event as a function of a number of carbohydrates the subject estimates will be in the prospective meal event. In some embodiments, the bolus insulin medicament dosage regimen 212 specifies a short acting insulin medicament dosage for a prospective meal event as a function of a number of carbohydrates the subject has historically consumed for the prospective meal event in the past.

In some embodiments, the long acting insulin medicament specified by the basal insulin medicament dosage regimen 208 consists of a single insulin medicament having a duration of action that is between 12 and 24 hours or a mixture of insulin medicaments that collectively have a duration of action that is between 12 and 24 hours. Examples of such long acting insulin medicaments include, but are not limited to, Insulin Degludec (developed by NOVO NORDISK under the brand name Tresiba), NPH (Schmid, 2007, "New options in insulin therapy," J Pediatria (Rio J). 83(Suppl 5): S146-S155), Glargine (LANTUS, Mar. 2, 2007), Insulin Glargine [rDNA origin] injection (Dunn et al. 2003, "An Updated Review of its Use in the Management of Diabetes Mellitus" Drugs 63: p. 1743), and Determir (Plank et al., 2005, "A double-blind, randomized, dose-response study investigating the pharmacodynamic and pharmacokinetic properties of the long-acting insulin analog detemir," Diabetes Care 28:1107-1112).

In some embodiments, the short acting insulin medicament specified by the bolus insulin medicament dosage regimen 212 comprises a single insulin medicament having a duration of action that is between three to eight hours or a mixture of insulin medicaments that collectively have a duration of action that is between three to eight hours. Examples of such short acting insulin medicaments include, but are not limited, to Lispro (HUMALOG, May 18, 2001, insulin lispro [rDNA origin] injection, Indianapolis, Ind.: Eli Lilly and Company), Aspart (NOVOLOG, July 2011, insulin aspart [rDNA origin] injection, Princeton, N.J., NOVO NORDISK Inc., July, 2011), Glulisine (Helms Kelley, 2009, "Insulin glulisine: an evaluation of its pharmacodynamic properties and clinical application," Ann Pharmacother 43:658-668), and Regular (Gerich, 2002, "Novel insulins: expanding options in diabetes management," Am J Med. 113:308-316).

Blocks 408-418. In block 408, a plurality of meal events within the time course encompassed by the first data set 218 are identified.

Referring to block 410, in some embodiments, meal events are identified using the plurality of autonomous glucose measurements and the corresponding timestamps in the first data set 218 in the time course encompassed by the first data set 218. In some such embodiments, the meal events are autonomously derived by analysis of the glucose measurements 222 in the first data set 220. For instance, referring to block 412, in some such embodiments, a meal event is detected from the autonomous glucose measurements 220 in the first data set 218 by computing: (i) a first model comprising a backward difference estimate of glucose rate of change using the autonomous glucose measurements 220, (ii) a second model comprising a backward difference estimate of glucose rate of change based on Kalman filtered estimates of glucose using the autonomous glucose measurements 220, (iii) a third model comprising a Kalman filtered estimate of glucose and Kalman filtered estimate of rate of change (ROC) of glucose based on the autonomous glucose measurements 220, and/or (iv) a fourth model comprising a Kalman filtered estimate of rate of change of ROC of glucose based on the plurality of autonomous glucose measurements 220. Referring to block 414, in some such embodiments, the first model, the second model, the third model and the fourth model are each computed across the autonomous glucose measurements 220 (meaning that all or a substantial portion of the autonomous glucose measurements 220 are used in the computation of the models) and a meal event is identified at an instance where at least three of the four models indicate a meal event. For further disclosure on such meal event detection, see Dassau et al., 2008, "Detection of a Meal Using Continuous Glucose Monitoring," Diabetes Care 31, pp. 295-300, which is hereby incorporated by reference. See also, Cameron et al., 2009, "Probabilistic Evolving Meal Detection and Estimation of Meal Total Glucose Appearance," Journal of Diabetes Science and Technology 3(5), pp. 1022-1030, which is hereby incorporated by reference.

Referring to block 418, in some embodiments, the identifying the plurality of meal events that occur during the time course comprises receiving a plurality of feed-forward events. Each respective feed-forward event in the plurality of feed-forward events represents an instance where the subject has indicated they are having or are about to have a meal. In some embodiments, both an autonomous meal detection algorithm, such as one disclosed in blocks 410 through 416, and the manual meal detection algorithm are used for meal detection. For instance, in some embodiments, the meals autonomously detected are verified using the feed-forward events. As an example, when a meal autonomously detected using an algorithm such as one disclosed in blocks 410 through 416 is matched in time (temporally matched) to a feed-forward event in which the subject indicated they are having a meal, the meal is deemed verified and used in further steps of the present disclosure.

Block 420. In block 420 of FIG. 4B, a second data set 224 is obtained that specifies, for each respective meal event 226 in the plurality of meal events, when a bolus insulin medicament dosage 214 was injected by the subject relative to an occurrence of the respective meal event.

Figure 9:
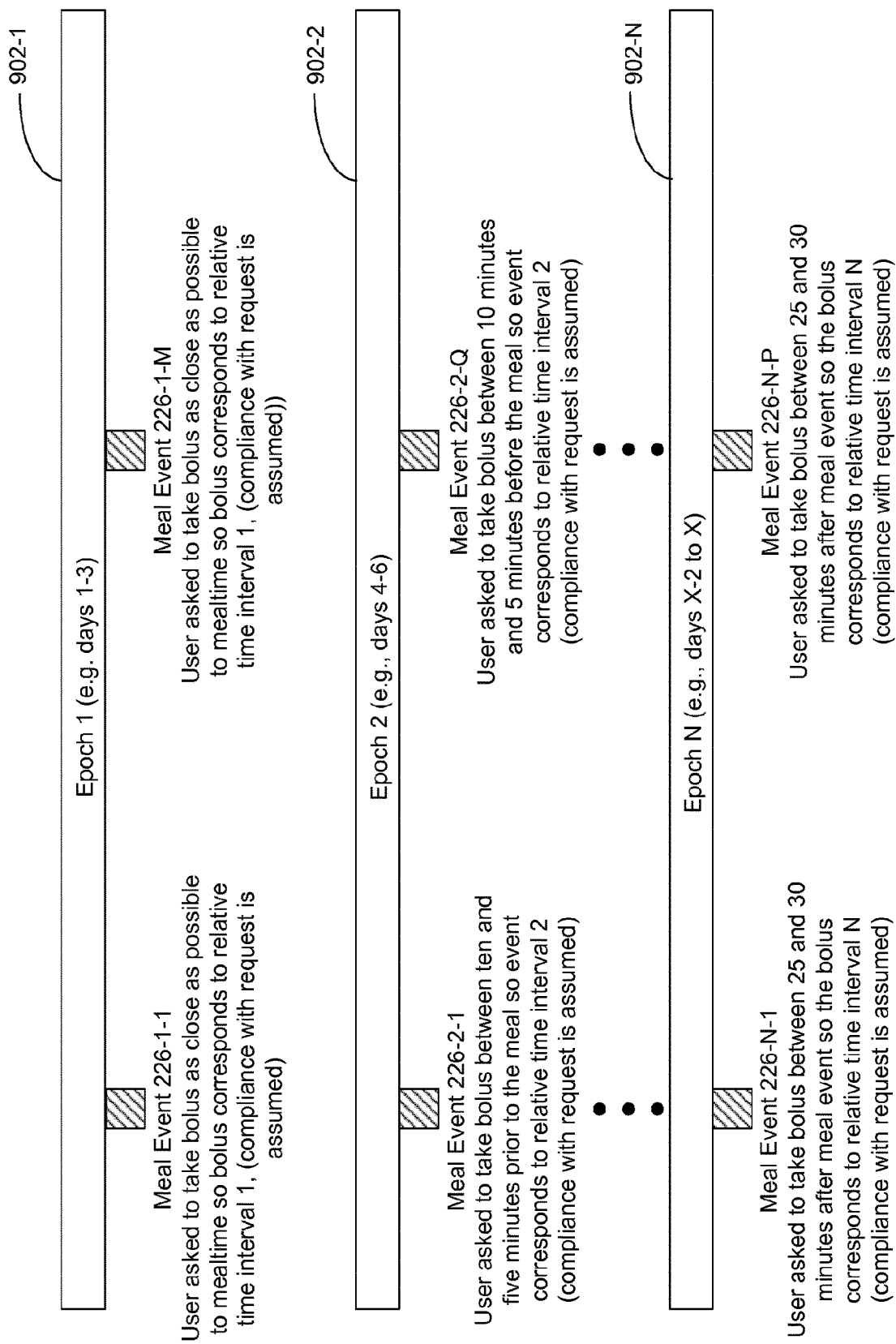
FIG. 9 illustrates an embodiment in which the information regarding the timing of bolus insulin medicament injection events is not available and subjects are asked to take a bolus insulin medicament injection at one of several different relative time periods at each epoch in a plurality of epochs in order to optimize a timing of a short acting insulin medicament dosage in a prescribed insulin regimen for a subject.

Referring to FIG. 9, in some embodiments information on when or whether short acting (bolus) insulin doses are taken is not available. In such embodiments, in order to determine optimal timing of dose, the subject is asked to take short acting insulin doses at varying times during a learning phase. In one example, the subject is asked to take a dose as close to meal start as possible. This is used as a reference. The patient is asked to do so for a period of time (an epoch), such as three days 902-1, to gain experience and account for daily variance in meal sizes, etc. After three days, a new epoch 902-2 is initiated, lasting another three days in which the subject is asked to take the bolus insulin dose five to ten minutes earlier, relative to each meal, than the prior epoch (the last three days). If hypoglycaemia is experienced, the learning phase is terminated and will not proceed to testing injection timings before meal time. If no hypoglycaemia is experienced, the algorithm will proceed with changing the suggested injection time by 5-10 minutes every three days, until reaching a limit, such as 30 minutes prior to meal ingestion. Next the subject is asked to similarly change the dosing every three days, but now after starting meal ingestion. Every three days the subject is asked to postpone the bolus medicament injection time by 5-10 minutes relative to the meal. This proceeds until the insulin is injected up to 30 minutes after meal ingestion. The three day period is just one example of an epoch, or period during which the subject is taking the bolus insulin injection at the same fixed predetermined period of time relative to each meal event. The epoch can be longer or shorter, for instance between one day and two weeks. FIG. 9 illustrates such a learning phase in which the epoch is defined as a three days. Each epoch, the user is asked to take the bolus injection at a different relative time in relation to a meal event during the time course over which the first data set is obtained.

Figure 10:
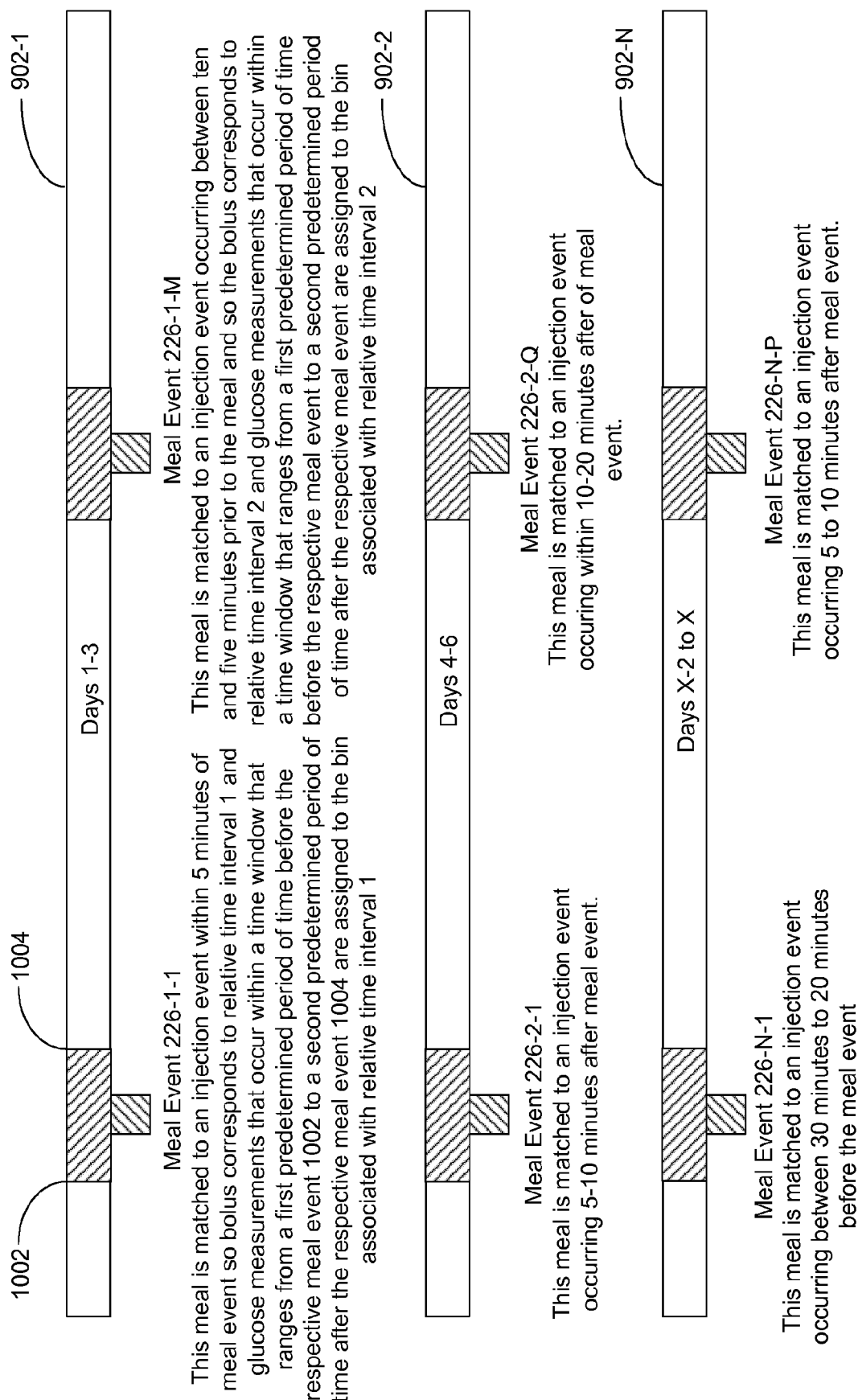
FIG. 10 illustrates an embodiment in which the information regarding the timing of bolus insulin medicament injection events is available and is autonomously matched to the timing of corresponding meal events in order to optimize a timing of a short acting insulin medicament dosage in a prescribed insulin regimen for a subject.

Referring to FIG. 10, in some embodiments, each such bolus injection event is determined by pen injection data received from the one or more insulin pens 104. In some alternative embodiments, bolus injection events are entered by a subject into device 250 manually upon occurrence. Regardless of their source, in such embodiments, bolus injection events include or are assigned a bolus insulin medicament dosage timestamp 228 that indicates when they occur and such timestamps 228 are used to temporally match the bolus injection to a corresponding meal event 226. In some embodiments a bolus injection event is deemed to temporally match a meal event 226 when they are within 40 minutes of each other, within 30 minutes of each other, or within 20 minutes of each other. In the example illustrated in FIG. 10, the subject is not asked to take a dose at particular times relative to meals as was the case in FIG. 9. Rather, in some embodiments the subject is asked to vary the relative bolus dosage time and in other embodiments the subject is simply provided with general guidance on a suitable overall relative time frame relative to a meal in which to make the bolus insulin medicament injection. Thus, each meal event 226 is independently analyzed for a temporally matching (corresponding) bolus injection event and the relative time between when the meal event and the corresponding bolus injection event took place is determined. Thus, whereas in FIG. 9 each epoch contained the same relative time between the bolus event and the corresponding meal event, in the embodiment illustrated in FIG. 10, it is possible for each meal within an epoch to have a substantially different relative time between when the bolus insulin medicament injection took place and when the corresponding meal event took place. For the embodiments illustrated in FIGS. 9 and 10, each respective bin is associated with an interval of different relative times in which the subject took the short acting insulin medicament dosage relative to the meal. For the embodiment relating to FIG. 9, an epoch, e.g., epoch 1, comprises a number of meal events and the subject has injected medicament dosage within a relative time interval to the meal events, and according to the instructions for the epoch, therefore it assumed that all the meal events within the same epoch are associated with the same relative time interval between a dosage injection time and a meal event, and therefore belong to the same bin. For the embodiment relating to FIG. 10, the injection of medicament dosages relative to meals are not limited to be injected within the same relative time for consecutive meals, instead the relative time between injection and meal may vary for consecutive meal events, and consecutive meal events may belong to different bins characterized by different intervals of relative times between injection and meal event. Some consecutive meal events may coincidently belong to the same relative time interval between injection and meal event, but the subject is not instructed to inject within one specific relative time interval.

For the embodiments relating to FIGS. 9 and 10, a first data set 218 is obtained, the first data set comprises a plurality of autonomous glucose measurements of the subject taken over a time course and, for each respective glucose measurement 220 in the plurality of glucose measurements, a corresponding timestamp 222 representing when in the time course the respective glucose measurement was made.

For the embodiments relating to FIGS. 9 and 10, the identifying a plurality of meal events in the first data set that occurred during the time course may further comprise applying an autonomous meal detection algorithm, such as the one disclosed in blocks 410 through 416, and/or applying the manual meal detection algorithm by, e.g., using feedforward events or by manually indicating, when the meal is ingested.

Therefore, for the embodiments relating to FIG. 9, a second data set 224 is obtained that specifies, for each respective meal event 226 in the plurality of meal events, when a short acting insulin medicament dosage was injected by the subject relative to an occurrence of the respective meal event, wherein the second data set 224 is based on a user injecting dosages according to the instruction of injecting a medicament dosage relative to a meal event within a specified interval for the relative time, wherein the specified interval is the same for a given epoch.

As a different approach, for the embodiments relating to FIG. 10, a second data set 224 is obtained that specifies, for each respective meal event 226 in the plurality of meal events, when a short acting insulin medicament dosage was injected by the subject relative to an occurrence of the respective meal event, wherein the second data set 224 is based on a user injecting dosages according to the instruction of injecting a medicament dosage relative to a meal event, wherein the relative time of injecting a medicament dosage relative to the meal event may increase and/or decrease for consecutive meal events, i.e., they may vary up and down in a non-specified pattern.

For the embodiments relating to FIGS. 9 and 10, the first data set is segmented into a plurality of segments, wherein each segment comprises glucose measurements that are associated with a period related to a meal event of the plurality of meal events.

The glucose measurements associated with a period related to a meal event, are defined by a period preceeding and/or following the meal event. The period can also include the time of injecting a dosage of medicament. As an example, the meal event is 12:00 and the assigned glucose measurements are obtained from a period including 12:00 and/or following 12:00, e.g. the period could be 11:30-14:30, 11:50-12:50, 12:00-15:00 or 12:10-14:10. The more measurements the period includes from an associated dosage and meal event the better. However, it is also important that measurements, relating to different relative time intervals between dosage and meal events, do not overlap too much. Preferably measurements relating to different relative time intervals between dosage and meal event, do not overlap.

For the embodiments relating to FIGS. 9 and 10, the plurality of segments of the first data set are binned into a plurality of bins using the second data set, and each respective segment, which is associated with a respective meal event, is binned by determining when the short acting insulin medicament dosage was injected by the subject relative to the occurrence of the respective meal event, wherein each respective bin 234 in the plurality of bins is associated with a relative time interval 236 in a plurality of relative time intervals. For the plurality of bins, each respective relative time interval in the plurality of relative time intervals defines a different time range for when a short acting insulin medicament dosage was injected by the subject relative to a meal event, and each respective bin is assigned segments comprising glucose measurements in the plurality of glucose measurements that are associated with one or more periods within the time course that are related to a respective meal event, in which the subject took the short acting insulin medicament dosage within the relative time interval associated with the respective bin. In the embodiments, a first glycaemic risk measure 238 is determined for each respective bin in the plurality of bins using the autonomous glucose measurements assigned to the respective bin, thereby a plurality of first glycaemic risk measures are formed. From among the plurality of relative time intervals associated with the plurality of bins, an optimal relative time interval, for the subject is identified, as the optimal relative time interval for injecting the short acting insulin medicament dosage for a prospective meal event, by using the plurality of first glycaemic risk measure. The optimal relative time interval is communicated to a health care practitioner associated with the subject or directly to the subject.

For the embodiments relating to FIG. 9, the method may further comprise validating that the user has injected the dosage relative to the meal event within the specified interval, by autonomous injection detection, and autonomous meal detection based on the plurality of glucose measurements in the first data set, i.e., both insulin injection and meal ingestion are associated with a change in the glucose level, which can be autonomously detected.

For the embodiments relating to FIG. 10, the step of obtaining the second data set may further comprise identifying each respective meal event 226 in the plurality of meal events in the first data set, by autonomous meal detection, and the associated injection event with a short acting insulin medicament in the first data set, by autonomous injection detection, and thereby obtaining when the dosage was injected by the subject relative to the occurrence of the respective meal event. Both insulin injection and meal ingestion are associated with a change in the glucose level, which can be autonomously detected.

Block 422. In block 422 of FIG. 4C, the first data set is segmented into a plurality of bins using the second data set, where each respective bin 234 in the plurality of bins is associated with a relative time interval 236 in a plurality of relative time intervals, each respective relative time interval in the plurality of relative time intervals defining a different time range for when a bolus insulin medicament dosage was injected by the subject relative to a meal event. In other words, the first data set is segmented, which means that a plurality of segments of the first data set are defined, wherein a segment is a plurality of measurements defined by a specified time period. Next the plurality of segments are put into or binned into a plurality of bins, which means that each segment is associated with a bin depending on a common characteristic between the segment and the bin. Each bin is characterized by a relative time interval defining a different time range for when a bolus insulin medicament dosage was injected relative to a meal. As each segment is associated with a meal, and each meal is associated with a dosage, each segment is characterized by a relative time between when the medicament dosage was injected and when the meal was ingested. The specified time period can be a period including and/or following the time of the meal event, or the period can also include the time of injecting the dosage. In one example, the plurality of relative time intervals comprises a first relative time interval ranging from 30 minutes to 25 minutes before a meal event, a second relative time interval ranging from 25 minutes to 20 minutes before a meal event, a third relative time interval ranging from 20 minutes to 15 minutes before a meal event, a fourth relative time interval ranging from 15 minutes to 10 minutes before a meal event, a fifth relative time interval ranging from 10 minutes to 5 minutes before a meal event, a sixth relative time interval ranging from 5 minutes to zero minutes before a meal event, a seventh relative time interval ranging from 0 minutes to 5 minutes after a meal event, an eighth relative time interval ranging from 5 minutes to 10 minutes after a meal event, a ninth relative time interval ranging from 10 minutes to 15 minutes after a meal event, a tenth relative time interval ranging from 15 minutes to 20 minutes after a meal event, an eleventh relative time interval ranging from 25 minutes to 25 minutes after a meal event, and a twelve relative time interval ranging from 25 minutes to 30 minutes after a meal event. In another example, the plurality of relative time intervals comprises a first relative time interval ranging from 30 minutes to 20 minutes before a meal event, a second relative time interval ranging from 20 minutes to 10 minutes before a meal event, a third relative time interval ranging from 10 minutes to 0 minutes before a meal event, a fourth relative time interval ranging from 0 minutes to 10 minutes after a meal event, a fifth relative time interval ranging from 10 minutes to 20 minutes before a meal event, and a sixth relative time interval ranging from 20 minutes to 30 minutes after a meal event.

In some embodiments the plurality of relative time intervals collectively span from 30 minutes to 30 minutes after corresponding meal events as in the examples disclosed above. In some embodiments the plurality of relative time intervals collectively span from 50 minutes to 50 minutes after corresponding meal events. In some embodiments the plurality of relative time intervals collectively span anywhere from 60 minutes to 60 minutes after corresponding meal events.

In some embodiments each relative time interval 236 has an internal time span of five minutes or ten minutes as in the examples disclosed above. In some embodiments each relative time interval 236 has the same internal time span that is between two minutes and ten minutes. For instance, in some embodiments, each relative time interval 236 in the plurality of relative time intervals is 3 minutes. As another example, in some embodiments, each relative time interval 236 in the plurality of relative time intervals is 6 minutes.

Each respective bin 234 is assigned glucose measurements 220 in the plurality of glucose measurements of the first data set 218 that are associated with one or more periods within the time course in which the subject took the bolus insulin medicament dosage 214 within the relative time interval 236 associated with the respective bin. For instance, referring to FIG. 9, there is a first bin 234-1 for the glucose measurements 220 taken during epoch 1, a second bin 234-2 for the glucose measurements 220 taken during epoch 2, and so forth. Referring to FIG. 10, there is a first bin 234-1 for the relative time interval 236-1 and the glucose measurements 220 associated with meal events (regardless of epoch) having a corresponding short acting insulin medicament dosage 214 within the relative time interval 236-1 are placed in the first bin, there is a second bin 234-2 for the relative time interval 236-2 and the glucose 220 measurements associated with meal events 226 (regardless of epoch) having a corresponding short acting insulin medicament dosage 214 within the relative time interval 236-2 are placed in the second bin, and so forth.

Blocks 424-438. Referring to block 424 of FIG. 4C, the method continues with a determination of a first glycaemic risk measure 238 for each respective bin 234 in the plurality of bins using the autonomous glucose measurements 220 assigned to the respective bin, thereby forming a plurality of first glycaemic risk measures.

Figure 4A:
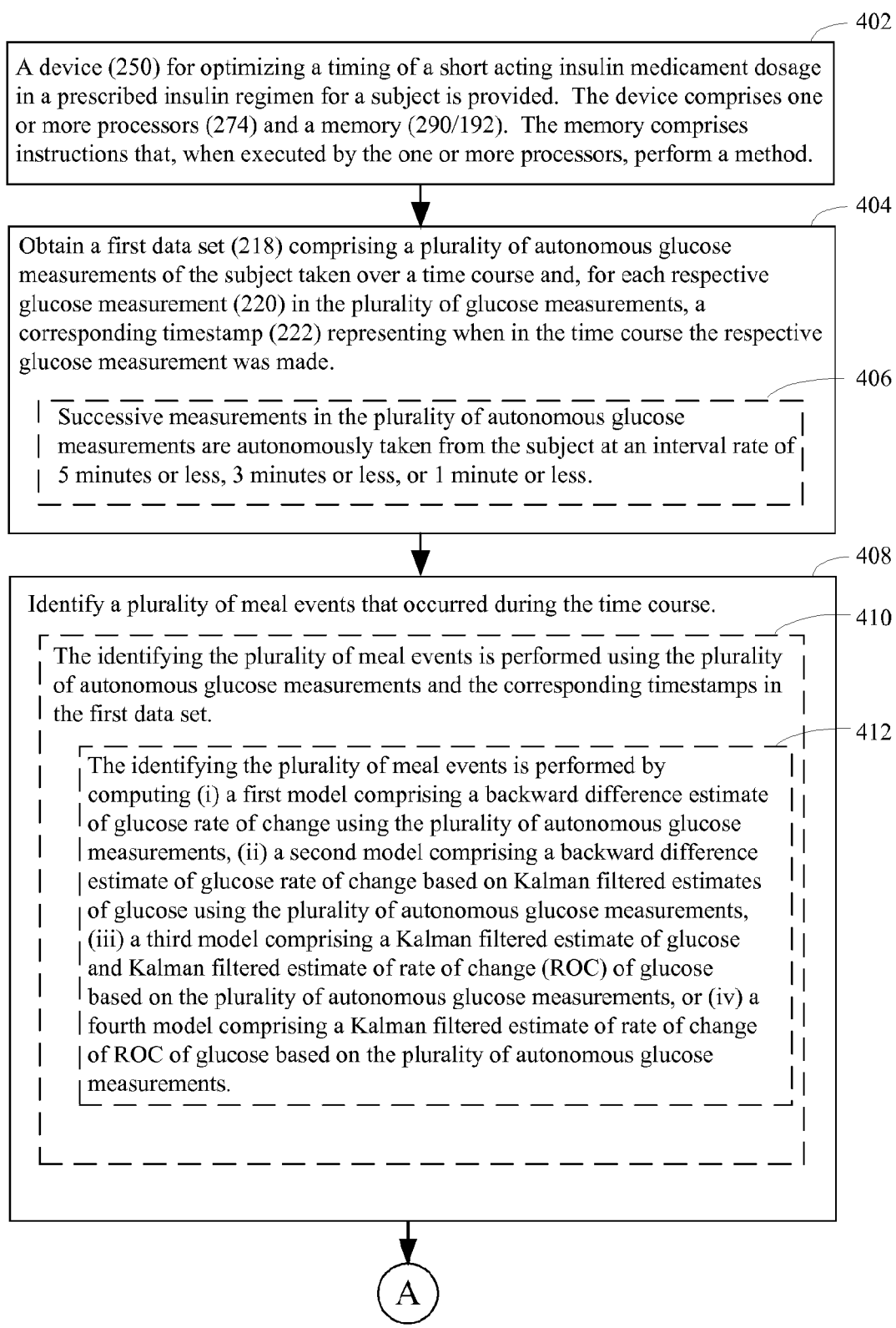
Figure 4B:
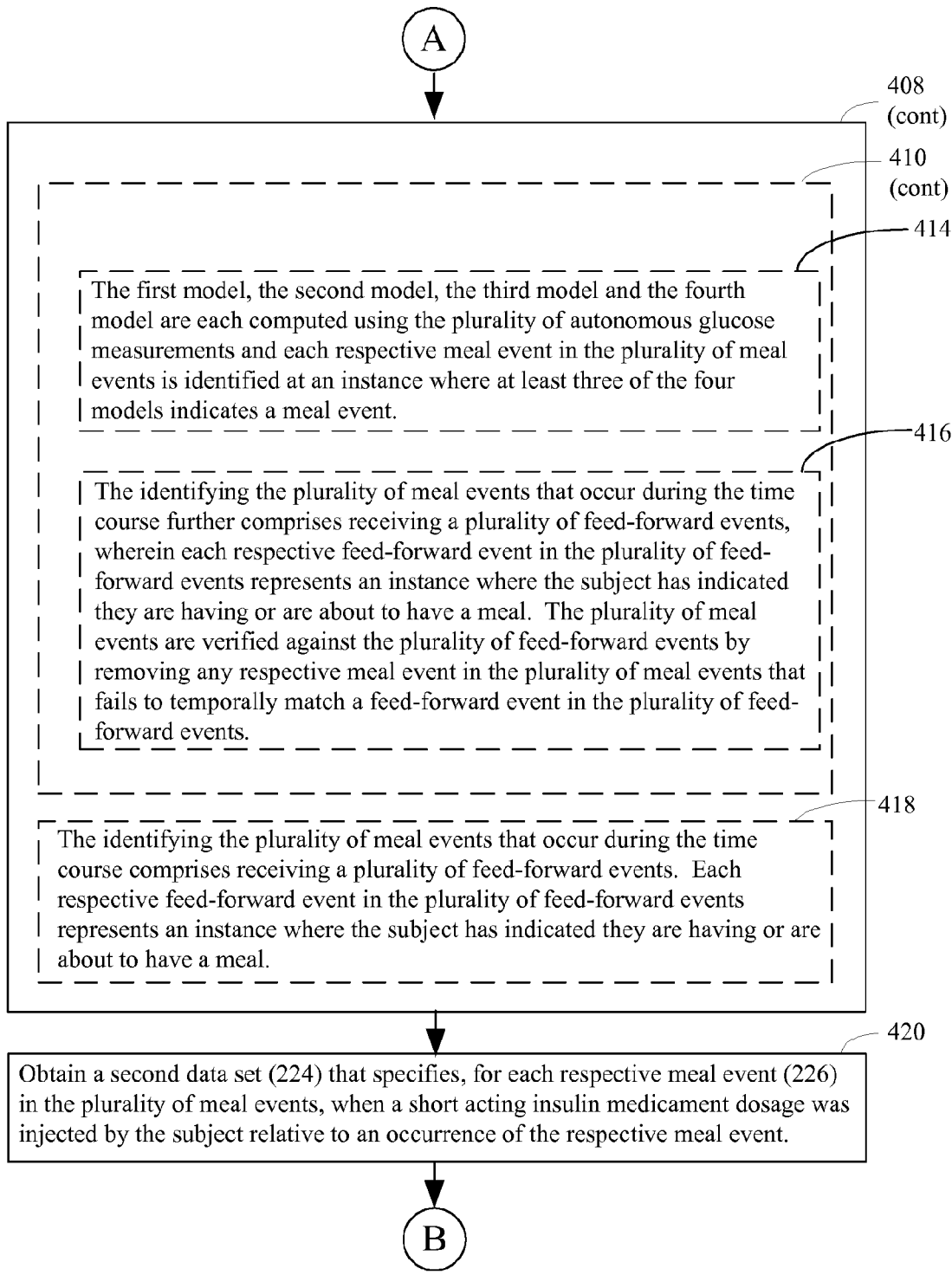
Figure 6:
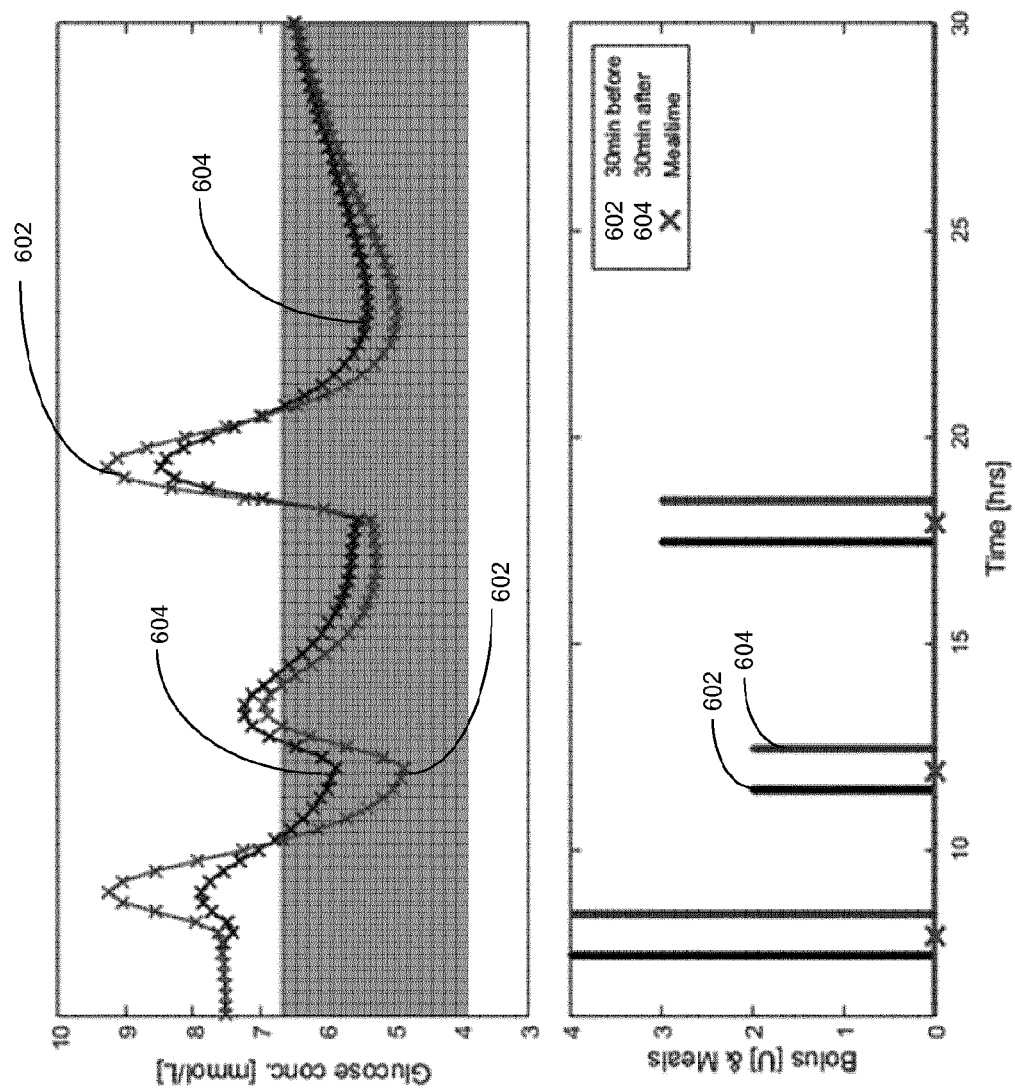
FIG. 6 illustrates how timing of a bolus injection relative to a meal event affects glycaemic control. When a bolus injection is taken 30 minutes before the meal is ingested, the variance in blood glucose and time spent above target is less than if the bolus is taken 30 minutes after meal ingestion.

Referring to block 426 of FIG. 4A, in some embodiments the first glycaemic risk measure 238 is calculated for a respective bin in the plurality of bins as: (i) a percentage of the time the glucose level of the subject is above a first target range across the glucose measurements assigned to the respective bin, (ii) a percentage of the time the glucose level of the subject is below the first target range across the glucose measurements assigned to the respective bin, (iii) a percentage of the time the glucose level of the subject is outside the first target range in the glucose measurement assigned to the respective bin, (iv) a measure of spread of the glucose measurements assigned to the respective bin, (v) a minimum glucose level in the glucose measurements assigned to the respective bin, or (vi) a maximum glucose level in the glucose measurements assigned to the respective bin. FIG. 6 illustrates. In FIG. 6, lower panel, there are two bins, bin 602 representing the injection of a bolus insulin medicament dosage 30 minutes prior to a meal, and bin 604 representing the injection of a bolus insulin medicament dosage 30 minutes after a meal. Glucose measurements for periods in the first time course associated with the relative time interval 30 minutes prior to a meal are plotted as line 602 in the upper panel of FIG. 6, whereas glucose measurements for periods in the first time course associated with the relative time interval 30 minutes after a meal are plotted as line 604 in the upper panel of FIG. 6. From the upper panel, a first glycaemic risk measure 238 can be calculated for respective bins 602 and 604. For instance, using FIG. 6 upper panel to illustrate, the percentage of the time the glucose level of the subject is above a first target range of 4.0 mmol/L to 6.8 mmol/L across the glucose measurements assigned to the respective bins 602 and 604 may be calculated and used as a first glycaemic risk measure 238, (ii) a percentage of the time the glucose level of the subject is below the first target range of 4.0 mmol/L to 6.8 mmol/L across the glucose measurements assigned to the respective bins 602 and 604 may be calculated and used as a first glycaemic risk measure 238, (iii) a percentage of the time the glucose level of the subject is outside (above or below) the first target range of 4.0 mmol/L to 6.8 mmol/L in the glucose measurement assigned to the respective bins 602 and 604 may be calculated and used as a first glycaemic risk measure 238, (iv) a measure of spread (e.g., delta between the highest level and lowest level) of the glucose measurements assigned to the respective bins 602 and 604 may be calculated and used as a first glycaemic risk measure 238, (v) a minimum glucose level in the glucose measurements assigned to the respective bins 602 and 604 may be calculated and used as a first glycaemic risk measure 238, or (vi) a maximum glucose level in the glucose measurements assigned to the respective bins 602 and 604 may be calculated and used as a first glycaemic risk measure 238. In some embodiments, the target range is different for each subject and is included, for instance, in the prescribed insulin regimen. For instance, in some embodiments the target range is individualized based on (i) duration of diabetes age, (ii) life expectancy, (iii) comorbid conditions, (iv) known CVD or advanced microvascular complications, and/or (v) hypo-glycaemia unawareness.

In some embodiments, only glucose measurements in each bin occurring prior to a corresponding meal (preprandial glucose measurements) are used to compute the first glycaemic risk measure 238. In some embodiments, only glucose measurements in each bin occurring after a corresponding meal (Postpreprandial glucose measurements) are used to compute the first glycaemic risk measure 238. In some embodiments, all glucose measurements in each bin, regardless of whether they occur before or after a corresponding meal are used to compute the first glycaemic risk measure 238.

Referring to block 428, in some embodiments, the first glycaemic risk measure 238 for a respective bin 234 is calculated as the total glucose level variability observed across the glucose measurements 220 (preprandial glucose measurements, postpreprandial glucose measurements, or both the preprandial glucose measurements and postpreprandial glucose measurements) in a respective bin. In more detail, in some embodiments, the first glycaemic risk measure 238 computed for a respective bin 234 is the total glucose level variability observed across the glucose measurements of the bin computed as one of (i), (ii), (iii), (iv) or (v): (i) a range of total glucose levels in the glucose measurements in the respective bin, (ii) an interquartile range of glucose levels in the plurality of glucose measurements in the respective bin, (iii) a variance of the glucose levels in the glucose measurements assigned to the respective bin, (iv) an average squared difference of the glucose levels in the plurality of glucose measurements assigned to the respective bin from the mean ($\mu$) of the glucose levels of the glucose measurements assigned to the respective bin ($\sigma^2$) computed as:

$$\sigma^2 = \frac{\sum_{i}^{P}(m_i - \mu)^2}{P}$$

where $m_i$ is the glucose level of the $i^{th}$ glucose measurement assigned to the respective bin, and P is a number of glucose measurements assigned to the respective bin, and (v) a standard deviation of the glucose levels of the glucose measurements assigned to the respective bin computed as $\sqrt{\sigma^2}$. In some embodiments, the first glycaemic risk is computed as any combination of (i), (ii), (iii), (iv), and (v).

In some embodiments, the autonomous glucose measurements 220 are limited to glucose levels measured from the subject in the past four hours, the past twelve hours, the past 24 hours, the past two days, the past week, or the past two weeks. In other words, in some embodiments, the first time course is the past four hours, the past twelve hours, the past 24 hours, the past two days, the past week, or the past two weeks and only those glucose measurements 220 for the subject from the past four hours, the past twelve hours, the past 24 hours, the past two days, the past week, or the past two weeks are used for the first data set 218. In other embodiments, the first data set 228 has glucose measurements 220 for the subject for more than the past four hours, the past twelve hours, the past 24 hours, the past two days, the past week, or the past two weeks, but measurements that are older than the past four hours, the past twelve hours, the past 24 hours, the past two days, the past week, or the past two weeks are not binned or used to calculate the first glycaemic risk measure. In still other embodiments, older glucose measurements are binned and used to calculate the first glycaemic risk measure but such older glucose measurements are down-weighted when computing the first glycaemic risk measure.

Referring to block 430 and as illustrated in FIG. 9, and as further discussed above in conjunction with FIG. 9, in some embodiments, the time course comprises a plurality of epochs. Each epoch 902 corresponds to a relative time interval 236 in the plurality of relative time intervals. In these embodiments, the second data set 224 specifies the relative time interval 236 in the plurality of relative time intervals for each epoch in the plurality of epochs. The method further comprises sharing the second data set 224 with the subject prior to the time course to enable the subject to inject the bolus insulin medicament dosage 214 at times 216 specified by the second data set 224 relative to respective meal events 226 during the time course. In such embodiments, the segmenting of the first data set 218 comprises assigning, for each respective epoch in the plurality of epochs, all glucose measurements 220 in (occurring during) the respective epoch to the corresponding bin 234 in the plurality of bins specified for the respective epoch by the second data set 224. Further, in such embodiments, the determining the first glycaemic risk measure 238 of a respective bin 234 in the plurality of bin collectively uses autonomous glucose measurements 220 assigned to the respective bin. In some such embodiments, the plurality of relative time intervals consists of 3, 4, 5, 6, 7, 8, 9, or 10 discrete time intervals centered around the meal event reference and there are correspondingly 3, 4, 5, 6, 7, 8, 9, or 10 bins, one for each relative time interval 236 and also 3, 4, 5, 6, 7, 8, 9, or 10 epochs, one or each relative time interval 236. Referring to block 432, in some embodiments, each epoch is one week or less, five days or less, three days or less, two days or less, one day or less, or 12 hours or less.

Referring to block 434 of FIG. 4D, and as further illustrated in FIG. 10 and as further described above in conjunction with FIG. 10, in some embodiments, a third data set 302 is obtained (e.g., from an insulin pen 104 used by the subject to apply the prescribed insulin regimen 206). Referring to FIG. 3, the third data set 302 comprises a plurality of insulin medicament records over the time course. Each insulin medicament record 304 comprises (i) a respective insulin medicament injection event 306 representing an insulin medicament injection (e.g., of the short acting insulin medicament dosage 214 into the subject) using the insulin pen 104, and (ii) a corresponding electronic timestamp 308 generated by the pen 104 upon occurrence of the injection. In such embodiments, the obtaining the second data set 224 comprises temporally matching meal events 226 to insulin medicament records 304 thereby determining an actual time difference for when the short acting insulin medicament dosage 214 was injected by the subject for each meal event 226 relative to the meal event (e.g., as ascertained from the meal event timestamp 230 as compared to the insulin event timestamp 308). In such embodiments, the segmenting the first data set 218 comprises associating, for each respective meal event 226, a bin 234 in the plurality of bins with the respective meal event using the second data set 224. The associating matches (i) the actual time difference and (ii) a corresponding relative time interval in the plurality of relative time intervals. For example, if the actual time difference is 8 minutes (meaning that the short acting insulin medicament was taken 8 minutes prior to the meal event), the associating matches the meal event to a bin that encompasses a time difference of 8 minutes (e.g., a bin that encompasses respective meal events in which the insulin medicament was taken between 5 and 10 minutes prior to the respective meal events). For each respective assigned meal event, autonomous glucose measurements in the plurality of autonomous glucose measurements that occur within a time window that ranges from a first predetermined period of time before the respective meal event to a second predetermined period of time after the respective meal event, are assigned to the associated bin. For instance, referring to meal event 226-1-1 of FIG. 10, the meal event 226-1-1, the meal is matched to an injection event within 5 minutes of the meal event so the bolus (the short acting inulin medicament injection event) corresponds to relative time interval 236-1 and glucose measurements that occur within a time window that ranges from a first predetermined period of time before the respective meal event 1002 to a second predetermined period of time after the respective meal event 1004 are assigned to the bin associated with relative time interval 236-1. This is opposed to the embodiment illustrated in FIG. 10 in which the glucose measurements of the entire epoch are assigned to the corresponding relative time interval 236. In some embodiments, the first predetermined period of time before the respective meal event 1002 is 90 minutes prior the respective meal event, 60 minutes prior the respective meal event, or 30 minutes prior the respective meal event. In some embodiments, the first predetermined period of time before the respective meal event 1002 is between 120 and 30 minutes prior to the respective meal event. In some embodiments, the second predetermined period of time after the respective meal event 1002 is 90 minutes after the respective meal event, 60 minutes after the respective meal event, or 30 minutes after the respective meal event. In some embodiments, the second predetermined period of time after the respective meal event 1002 is between 30 and 120 minutes after the respective meal event. In typical embodiments, as illustrated in FIG. 10, the segmenting associates more than one meal event to each bin (e.g. meal event 226-2-1 and 226-N-P are both assigned to the same bin in FIG. 10). As was the case for the embodiment illustrated in FIG. 9, the determining the first glycaemic risk measure of a respective bin collectively uses the glucose measurements assigned to the bin.

Referring to block 436 of FIG. 4E, in some alternative embodiments, the method further comprises obtaining a third data set 310 from an insulin pen 104 used by the subject to apply the prescribed insulin regimen 206. In such embodiments, the third data set 302 comprises a plurality of insulin medicament records over the time course. Each insulin medicament record 304 in the plurality of medicament records comprises (i) a respective insulin medicament injection event representing an insulin medicament injection of the short acting insulin medicament dosage 214 into the subject using the insulin pen 104, and (ii) a corresponding electronic timestamp 308 that is automatically generated by the insulin pen 104 upon occurrence of the respective insulin medicament injection event. In such embodiments, the obtaining the second data set 224 comprises temporally matching respective meal events 226 in the plurality of meal events to respective insulin medicament records 304 thereby determining an actual time difference for when the bolus insulin medicament dosage 214 was injected by the subject for each respective meal event 226. Further, in such embodiments, the identifying the plurality of meal events further comprises applying a first characterization to each meal event in the plurality of meal events. The first characterization is one of insulin regimen adherent and insulin regimen nonadherent. In such embodiments, a respective meal event 226 is deemed insulin regimen adherent when one or more medicament records 304 in the plurality of medicament records has an insulin event timestamp 308 that is within a predetermined amount of time of the respective meal event. In some embodiments, this predetermined amount of time is 90 minutes or less, 60 minutes or less, or 30 minutes or less. In some embodiments, this predetermined amount of time is between 15 and 90 minutes. A respective meal event 226 is deemed insulin regimen nonadherent when no insulin medicament record 304 in the plurality of insulin medicament records has an insulin event timestamp 308 that is within the predetermined amount of time of the respective meal event. Further, in such embodiments, the segmenting the first data set comprises determining, for each respective meal event 226 in the plurality of meal events that is deemed insulin regimen adherent, which bin 234 in the plurality of bins is associated with the respective meal event 226 using the second data set 224 by a procedure. The procedure comprises matching when a short acting insulin medicament dosage 214 was injected by the subject relative to the respective meal event 226 to a corresponding relative time interval 236 in the plurality of relative time intervals, and assigning, for each respective meal event 226 in the plurality of meal events, autonomous glucose measurements 220 in the plurality of autonomous glucose measurements that occur within a time window that ranges from a first predetermined period of time before the respective meal event to a second predetermined period of time after the respective meal event, to the associated bin. In some embodiments, the first predetermined period of time before the respective meal event 226 is 90 minutes prior the respective meal event, 60 minutes prior the respective meal event, or 30 minutes prior the respective meal event. In some embodiments, the first predetermined period of time before the respective meal event 226 is between 120 and 30 minutes prior to the respective meal event. In some embodiments, the second predetermined period of time after the respective meal event 226 is 90 minutes after the respective meal event, 60 minutes after the respective meal event, or 30 minutes after the respective meal event. In some embodiments, the second predetermined period of time after the respective meal event 226 is between 30 and 120 minutes after the respective meal event. Further, in such embodiments, the segmenting associates more than one meal event 226 from the plurality of meal events to each bin 234 in the plurality of bins. Also in such embodiments, the determining the first glycaemic risk measure 238 of a respective bin 234 in the plurality of bins collectively uses the autonomous glucose measurements 220 assigned to the respective bin.

Figure 4F:
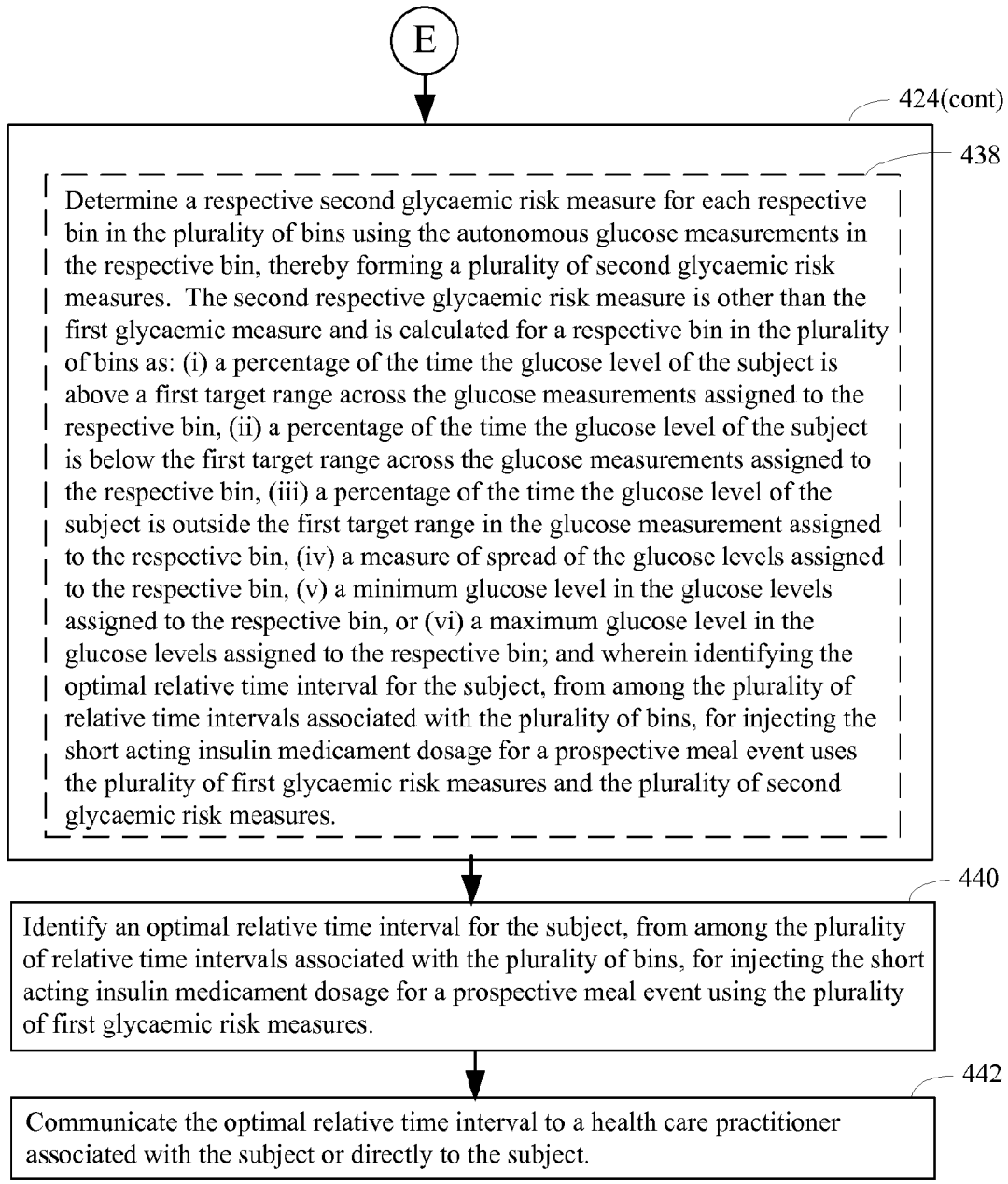

Referring to block 438 of FIG. 4F, in some embodiments, a respective second glycaemic risk measure is determined for each respective bin 234 in the plurality of bins using the autonomous glucose measurements 220 in the respective bin, thereby forming a plurality of second glycaemic risk measures. In some such embodiments, the second respective glycaemic risk measure is other than the first glycaemic measure and is calculated for a respective bin in the plurality of bins as: (i) a percentage of the time the glucose level of the subject is above a first target range across the glucose measurements assigned to the respective bin, (ii) a percentage of the time the glucose level of the subject is below the first target range across the glucose measurements assigned to the respective bin, (iii) a percentage of the time the glucose level of the subject is outside the first target range in the glucose measurement assigned to the respective bin, (iv) a measure of spread of the glucose levels assigned to the respective bin, (v) a minimum glucose level in the glucose levels assigned to the respective bin, or (vi) a maximum glucose level in the glucose levels assigned to the respective bin. Further, in such embodiments, the identifying the optimal relative time interval 236 for the subject, from among the plurality of relative time intervals associated with the plurality of bins, for injecting the short acting insulin medicament dosage 214 for a prospective meal event uses the plurality of first glycaemic risk measures and the plurality of second glycaemic risk measures. For instance, in some embodiments, the outcome of a first glycaemic risk measure for a respective bin 234 and the outcome of a second glycaemic risk measure for the respective bin 234 are optionally combined as a linear or nonlinear combination as a composite glycaemic risk measure for identifying which bin 234, and therefore which relative time interval 236 optimizes the composite glycaemic risk measures and/or the risk measures individually. In some embodiments, three or more glycaemic risk measures are computed for each respective bin and optionally combined into a composite glycaemic risk measure for the respective bin as a linear or nonlinear combination for identifying which bin, and therefore which relative time interval 236 optimizes the composite glycaemic risk measure or the glycaemic risk measures individually. In some embodiments, a set of glycaemic risk measures are computed for each respective bin and optionally combined into a composite glycaemic risk measure as a linear or nonlinear combination for identifying which bin, and therefore which relative time interval 236, optimizes the composite glycaemic risk measure and/or the glycaemic risk measure individually, where the set of glycaemic risk measures consists of 2, 3, 4, 5, 6, 7, 8, 9, or 10 or more glycaemic risk measures each calculated using data, such as the autonomous glucose measurements 220, assigned to the bin.

Block 440. In block 440, the method continues with the identification of an optimal relative time interval for the subject, from among the plurality of relative time intervals associated with the plurality of bins, for injecting the short acting insulin medicament dosage for a prospective meal event using the plurality of first glycaemic risk measures.

Figure 7A:
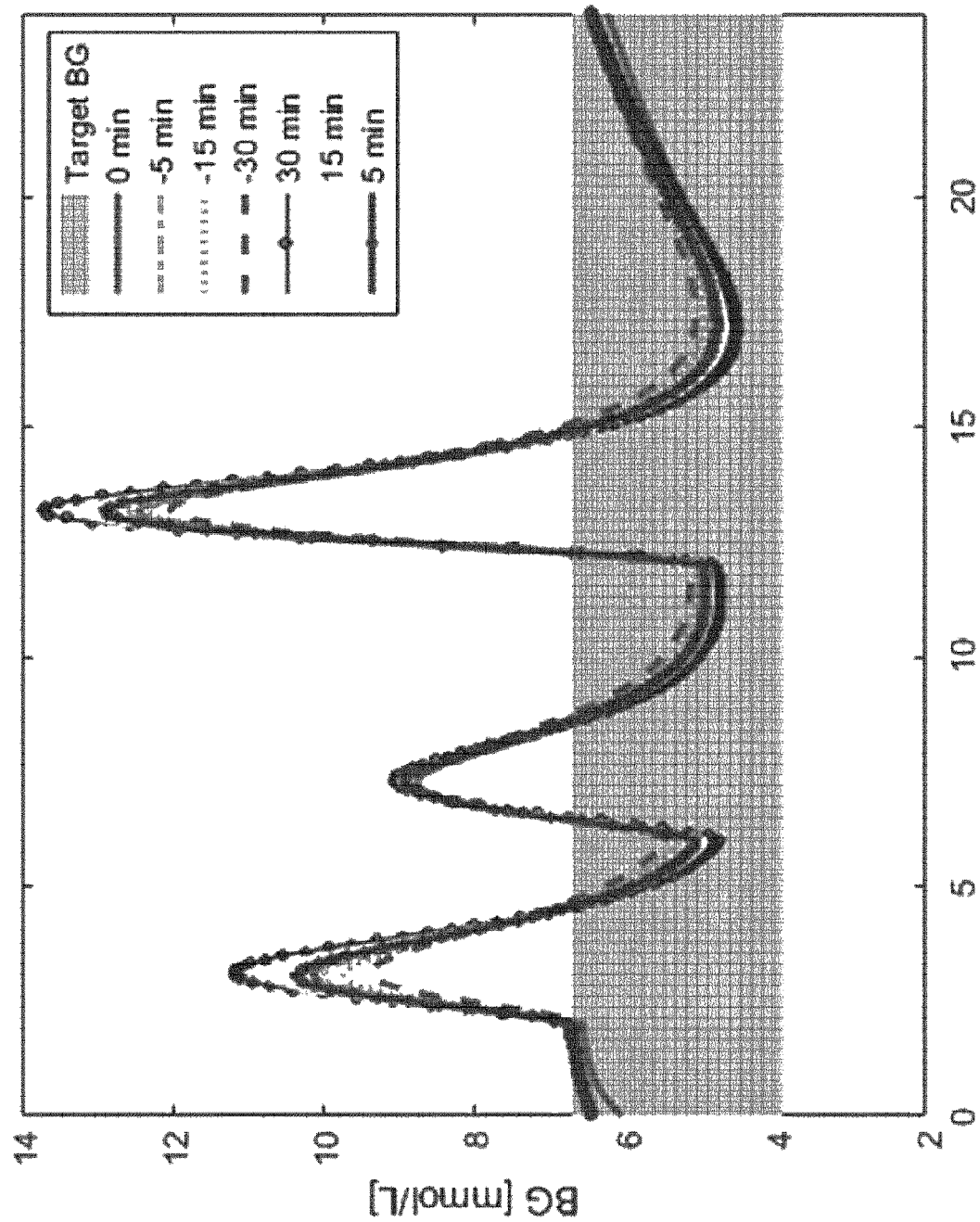
FIGS. 7A and 7B illustrate the results of determining optimal timing of a bolus injection for one patient, using only continuous glucose monitoring data in accordance with an embodiment of the present disclosure.
Figure 7B:
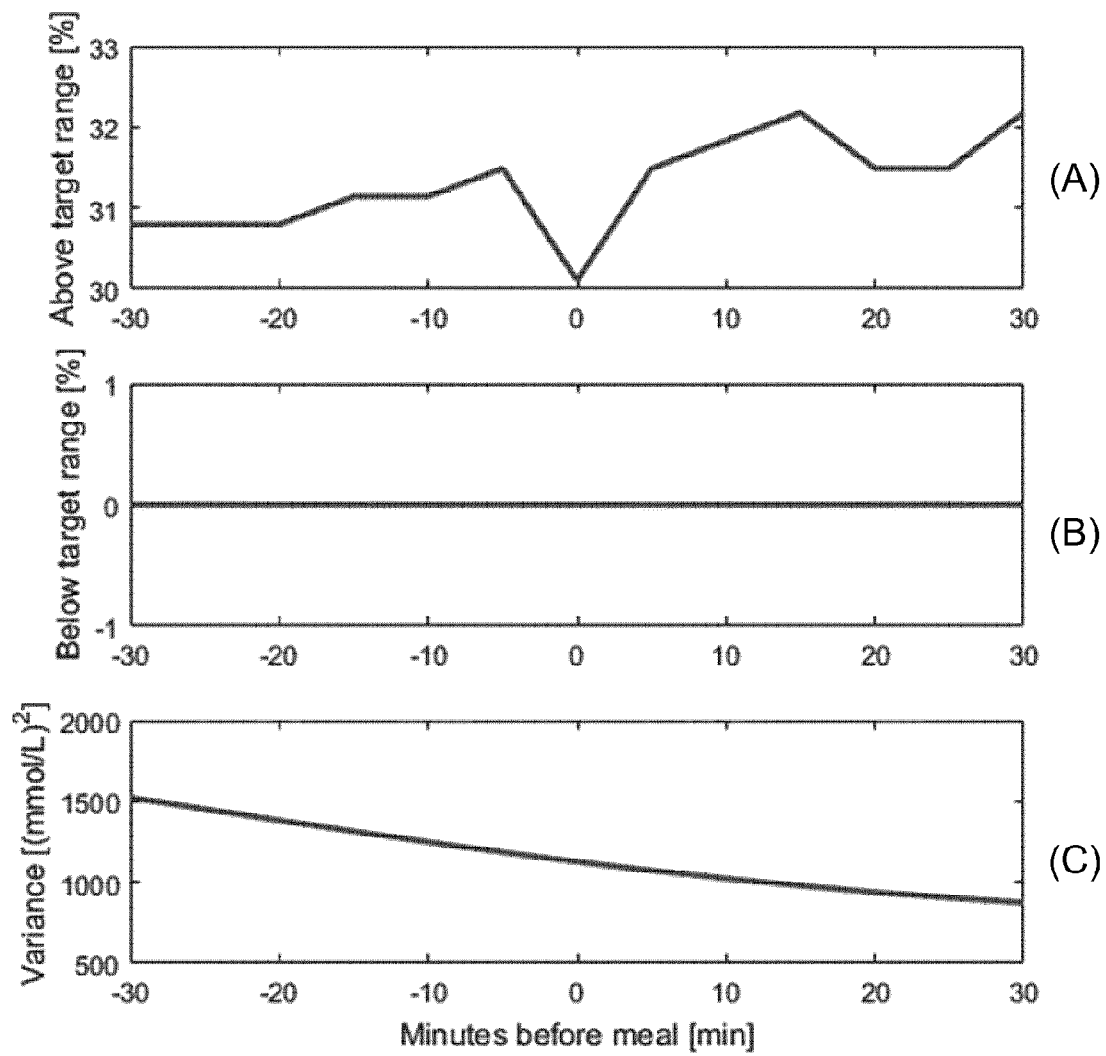
Figure 8A:
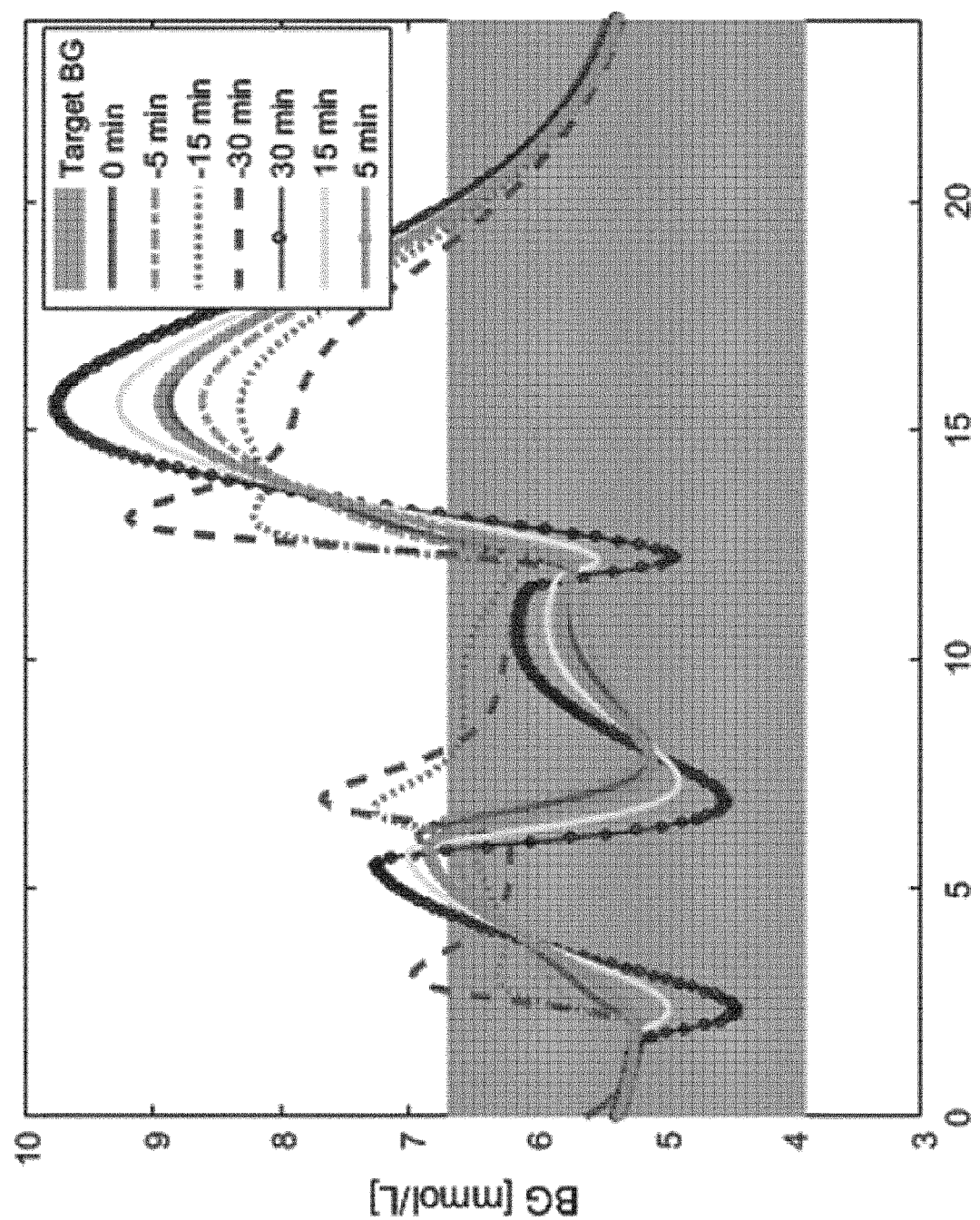
FIGS. 8A and 8B illustrate the results of determining optimal timing of a bolus injection in the same manner as FIGS. 7A and 7B for another patient in accordance with an embodiment of the present disclosure.
Figure 8B:
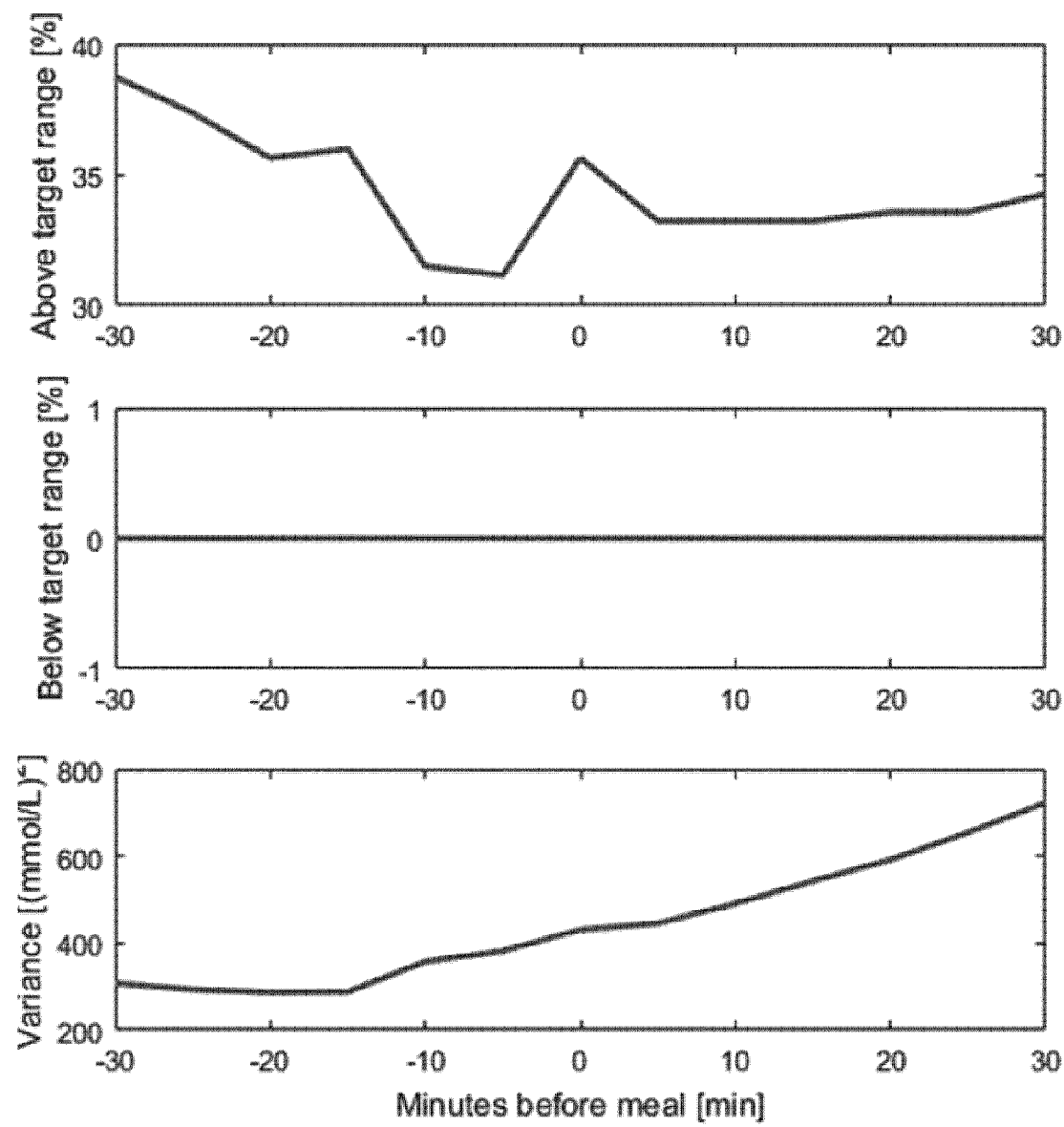

FIG. 7 illustrates with the case of determining optimal timing of bolus injection for one patient, using only the autonomous glucose measurements 220 of the first data set. FIG. 7A shows the average glucose concentration over seven epochs each having a respective duration of three days (epoch 1: relative time interval 236-1 is 0 minutes, epoch 2: relative time interval 236-1 is −5 minutes, epoch 3: relative time interval 236-1 is −15 minutes, epoch 4: relative time interval 236-1 is −30, epoch 5: relative time interval 236-1 is 30 minutes, epoch 6: relative time interval 236-1 is 15 minutes, and epoch 7: relative time interval 236-1 is 5). No registered meal or injection data is available. FIG. 7B illustrates the calculation of three glycaemic risk measures from each epoch. From the top of FIG. 7B, panel A shows the time spent in hyperglycaemia, panel B shows the time spent in hypoglycaemia, and panel C shows the daily variance in each epoch, where each epoch is represented on the x-axis by its characteristic relative time interval 236 (minutes from the reference meal event timing). In FIG. 7B, positive minutes indicate injection times before meal ingestion, and negative minutes indicate injection times after meal ingestion. The data for the subject of FIG. 7 indicates an optimal relative time interval 236 of 0 minutes. FIG. 8 illustrates the same results as presented in FIG. 7, except for another patient, and indicates an optimal relative time interval 236 of −10 minutes.

Block 442. In block 442, the method continues with the communication of an optimal relative time interval 236 to a health care practitioner associated with the subject or directly to the subject. Advantageously, communication of an optimal relative time interval 236 to the subject allows the subject to optimize the timing of their short acting insulin medicament dosage relative to meal events in between health care practitioner visits.

LIST OF EMBODIMENTS

1. A device 250 for optimizing a timing of a short acting insulin medicament dosage in a prescribed insulin regimen for a subject, wherein the device comprises one or more processors 274 and a memory 290/192, the memory comprising:

instructions that, when executed by the one or more processors, perform a method of:

obtaining a first data set 218, the first data set comprising a plurality of autonomous glucose measurements of the subject taken over a time course and, for each respective glucose measurement 220 in the plurality of glucose measurements, a corresponding timestamp 222 representing when in the time course the respective glucose measurement was made;

identifying a plurality of meal events in the first data set that occurred during the time course, and thereby specifying the occurrence of each of the plurality of meal events using the first data set;

obtaining a second data set 224 that specifies, for each respective meal event 226 in the plurality of meal events, when a short acting insulin medicament dosage was injected by the subject relative to an occurrence of the respective meal event;

segmenting the first data set into a plurality of segments, wherein each segment comprises glucose measurements that are associated with a period related to a meal event of the plurality of meal events;

binning the plurality of segments of the first data set into a plurality of bins using the second data set, wherein each segment, associated with a respective meal event, is binned by determining when the short acting insulin medicament dosage was injected by the subject relative to the occurrence of the respective meal event, wherein each respective bin 234 in the plurality of bins is associated with a relative time interval 236 in a plurality of relative time intervals, each respective relative time interval in the plurality of relative time intervals defines a different time range for when the short acting insulin medicament dosage was injected by the subject relative to the occurrence of the meal event, and each respective bin is assigned glucose measurements in the plurality of glucose measurements that are associated with one or more periods within the time course that are related to a meal event, in which the subject took the short acting insulin medicament dosage within the relative time interval associated with the respective bin;

determining a first glycaemic risk measure 238 for each respective bin in the plurality of bins using the autonomous glucose measurements assigned to the respective bin, thereby forming a plurality of first glycaemic risk measures;

identifying an optimal relative time interval for the subject, from among the plurality of relative time intervals associated with the plurality of bins, for injecting the short acting insulin medicament dosage for a prospective meal event using the plurality of first glycaemic risk measures; and communicating the optimal relative time interval to a health care practitioner associated with the subject or directly to the subject.

2. The device of embodiment 1, wherein the first glycaemic risk measure is calculated for a respective bin in the plurality of bins as:
   (i) a percentage of the time the glucose level of the subject is above a first target range across the glucose measurements assigned to the respective bin,
   (ii) a percentage of the time the glucose level of the subject is below the first target range across the glucose measurements assigned to the respective bin,
   (iii) a percentage of the time the glucose level of the subject is outside the first target range in the glucose measurement assigned to the respective bin,
   (iv) a measure of spread of the glucose measurements assigned to the respective bin,
   (v) a minimum glucose level in the glucose measurements assigned to the respective bin, or
   (vi) a maximum glucose level in the glucose measurements assigned to the respective bin.

3. The device of embodiment 1, wherein the first glycaemic risk measure is calculated for a respective bin in the plurality of bins as:
   (i) a range of the glucose measurements assigned to the respective bin,
   (ii) an interquartile range of glucose measurements assigned to the respective bin,
   (iii) a variance of the glucose measurements assigned to the respective bin,
   (iv) an average squared difference of the glucose measurements assigned to the respective bin from the mean ($\mu$) of the glucose measurements assigned to the respective bin ($\sigma^2$) computed as:

$$\sigma^2 = \frac{\sum_i^P (m_i - \mu)^2}{P}$$

wherein,
      $m_i$ is the $i^{th}$ glucose measurement assigned to the respective bin, and
      P is a number of glucose measurements assigned to the respective bin, or
   (v) a standard deviation of the glucose measurements assigned to the respective bin computed as $\sqrt{\sigma^2}$.

4. The device of embodiment 1, wherein the identifying the plurality of meal events is performed using the plurality of autonomous glucose measurements and the corresponding timestamps in the first data set.

5. The device of embodiment 4, wherein the identifying the plurality of meal events is performed by computing:
   (i) a first model comprising a backward difference estimate of glucose rate of change using the plurality of autonomous glucose measurements,
   (ii) a second model comprising a backward difference estimate of glucose rate of change based on Kalman filtered estimates of glucose using the plurality of autonomous glucose measurements,
   (iii) a third model comprising a Kalman filtered estimate of glucose and Kalman filtered estimate of rate of change (ROC) of glucose based on the plurality of autonomous glucose measurements, or
   (iv) a fourth model comprising a Kalman filtered estimate of rate of change of ROC of glucose based on the plurality of autonomous glucose measurements.

6. The device of embodiment 5, wherein the first model, the second model, the third model and the fourth model are each computed using the plurality of autonomous glucose measurements and each respective meal event in the plurality of meal events is identified at an instance where at least three of the four models indicates a meal event.

7. The device of any one of embodiments 4-6, wherein the identifying the plurality of meal events that occur during the time course further comprises receiving a plurality of feed-forward events, wherein each respective feed-forward event in the plurality of feed-forward events represents an instance where the subject has indicated they are having or are about to have a meal, and
   the plurality of meal events are verified against the plurality of feed-forward events by removing any respective meal event in the plurality of meal events that fails to temporally match a feed-forward event in the plurality of feed-forward events.

8. The device of embodiment 1, wherein the identifying the plurality of meal events that occur during the time course comprises receiving a plurality of feed-forward events, wherein each respective feed-forward event in the plurality of feed-forward events represents an instance where the subject has indicated they are having or are about to have a meal.

9. The device of embodiment 1, wherein
   the time course comprises a plurality of epochs, each epoch corresponding to a relative time interval in the plurality of relative time intervals;
   the second data set specifies the relative time interval in the plurality of relative time intervals for each epoch in the plurality of epochs; and wherein the method further comprises:
   sharing the second data set with the subject prior to the time course to enable the subject to inject the short acting insulin medicament dosage at times specified by the second data set relative to respective meal events during the time course, and wherein
   the segmenting the first data set comprises assigning, for each respective epoch in the plurality of epochs, all glucose measurements in the respective epoch to the corresponding bin in the plurality of bins specified for the respective epoch by the second data set; and
   the determining the first glycaemic risk measure of a respective bin in the plurality of bin collectively uses autonomous glucose measurements assigned to the respective bin.

10. The device of embodiment 9, wherein each epoch in the plurality of epochs is one week or less, five days or less, three days or less, two days or less, one day or less, or 12 hours or less.

11. The device of embodiment 1, wherein the method further comprises:
obtaining a third data set 302 from an insulin pen used by the subject to apply the prescribed insulin regimen, the third data set comprising a plurality of insulin medicament records over the time course, each insulin medicament record 304 in the plurality of medicament records comprising:
(i) a respective insulin medicament injection event 306 representing an insulin medicament injection of the short acting insulin medicament dosage into the subject using the insulin pen, and
(ii) a corresponding electronic timestamp 308 that is automatically generated by the insulin pen upon occurrence of the respective insulin medicament injection event, and wherein
the obtaining the second data set comprises temporally matching respective meal events in the plurality of meal events to respective insulin medicament records thereby determining an actual time difference for when the short acting insulin medicament dosage was injected by the subject for each respective meal event relative to the respective meal event,
the segmenting the first data set comprises:
associating, for each respective meal event in the plurality of meal events, a bin in the plurality of bins with the respective meal event using the second data set, wherein the associating matches (i) the actual time difference and (ii) a corresponding relative time interval in the plurality of relative time intervals, and
assigning, for each respective meal event in the plurality of meal events, autonomous glucose measurements in the plurality of autonomous glucose measurements that occur within a time window that ranges from a first predetermined period of time before the respective meal event to a second predetermined period of time after the respective meal event, to the associated bin, and wherein the segmenting associates more than one meal event from the plurality of meal events to each bin in the plurality of bins, and
the determining the first glycaemic risk measure of a respective bin in the plurality of bins collectively uses autonomous glucose measurements assigned to the respective bin.

12. The device of embodiment 1, wherein the method further comprises:
obtaining a third data set 302 from an insulin pen 104 used by the subject to apply the prescribed insulin regimen, the third data set comprising a plurality of insulin medicament records over the time course, each insulin medicament record 304 in the plurality of medicament records comprising:
(i) a respective insulin medicament injection event 306 representing an insulin medicament injection of the short acting insulin medicament dosage 214 into the subject using the insulin pen, and
(ii) a corresponding insulin event timestamp 308 that is automatically generated by the insulin pen upon occurrence of the respective insulin medicament injection event, and wherein
the obtaining the second data set comprises temporally matching respective meal events in the plurality of meal events to respective insulin medicament records thereby determining an actual time difference for when the short acting insulin medicament dosage was injected by the subject for each respective meal event,
the identifying the plurality of meal events further comprises applying a first characterization to each meal event in the plurality of meal events, wherein the first characterization is one of insulin regimen adherent and insulin regimen nonadherent, wherein a respective meal event is deemed insulin regimen adherent when one or more insulin medicament records in the plurality of insulin medicament records has an insulin event timestamp that is within a predetermined amount of time of the respective meal event, and
a respective meal event is deemed insulin regimen nonadherent when no medicament record in the plurality of medicament records has an insulin event timestamp that is within the predetermined amount of time of the respective meal event,
the segmenting the first data set comprises:
determining, for each respective meal event in the plurality of meal events that is deemed insulin regimen adherent, which bin in the plurality of bins is associated with the respective meal event using the second data set by a procedure comprising:
matching when a short acting insulin medicament dosage was injected by the subject relative to the respective meal event to a corresponding relative time interval in the plurality of relative time intervals, and
assigning, for each respective meal event in the plurality of meal events, autonomous glucose measurements in the plurality of autonomous glucose measurements that occur within a time window that ranges from a first predetermined period of time before the respective meal event to a second predetermined period of time after the respective meal event, to the associated bin, and wherein the segmenting associates more than one meal event from the plurality of meal events to each bin in the plurality of bins, and
the determining the first glycaemic risk measure of a respective bin in the plurality of bins collectively uses autonomous glucose measurements assigned to the respective bin.

13. The device of any one of embodiments 1-12, wherein successive measurements in the plurality of autonomous glucose measurements are autonomously taken from the subject at an interval rate of 5 minutes or less, 3 minutes or less, or 1 minute or less.

14. The device of any one of embodiments 1-14, the method further comprising:
determining a respective second glycaemic risk measure for each respective bin in the plurality of bins using the autonomous glucose measurements in the respective bin, thereby forming a plurality of second glycaemic risk measures, wherein the second respective glycaemic risk measure is other than the first glycaemic measure and is calculated for a respective bin in the plurality of bins as:
(i) a percentage of the time the glucose level of the subject is above a first target range across the glucose measurements assigned to the respective bin,
(ii) a percentage of the time the glucose level of the subject is below the first target range across the glucose measurements assigned to the respective bin, (iii) a percentage of the time the glucose level of the subject is outside the first target range in the glucose measurement assigned to the respective bin, (iv) a measure of spread of the glucose measurements assigned to the respective bin, (v) a minimum glucose level in the glucose measurements assigned to the respective bin, or (vi) a maximum glucose level in the glucose measurements assigned to the respective bin; and wherein identifying the optimal relative time interval for the subject, from among the plurality of relative time intervals associated with the plurality of bins, for injecting the short acting insulin medicament dosage for a prospective meal event uses the plurality of first glycaemic risk measures and the plurality of second glycaemic risk measures.

15. A method for optimizing a timing of a short acting insulin medicament dosage in a prescribed insulin regimen for a subject, the method comprising:

at a computer comprising one or more processors and a memory:

obtaining a first data set, the first data set comprising a plurality of autonomous glucose measurements of the subject taken over a time course and, for each respective glucose measurement in the plurality of glucose measurements, a corresponding timestamp representing when in the time course the respective glucose measurement was made;

identifying a plurality of meal events in the first data set that occurred during the time course;

obtaining a second data set 224 that specifies, for each respective meal event 226 in the plurality of meal events, when a short acting insulin medicament dosage was injected by the subject relative to an occurrence of the respective meal event;

segmenting the first data set into a plurality of segments, wherein each segment comprises glucose measurements that are associated with a period related to a meal event of the plurality of meal events;

binning the plurality of segments of the first data set into a plurality of bins using the second data set, wherein each segment, associated with a respective meal event, is binned by determining when the short acting insulin medicament dosage was injected by the subject relative to the occurrence of the respective meal event, wherein each respective bin 234 in the plurality of bins is associated with a relative time interval 236 in a plurality of relative time intervals, each respective relative time interval in the plurality of relative time intervals defines a different time range for when a short acting insulin medicament dosage was injected by the subject relative to a meal event, and each respective bin is assigned glucose measurements in the plurality of glucose measurements that are associated with one or more periods within the time course that are related to a meal event, in which the subject took the short acting insulin medicament dosage within the relative time interval associated with the respective bin;

determining a first glycaemic risk measure for each respective bin in the plurality of bins using the autonomous glucose measurements assigned to the respective bin, thereby forming a plurality of first glycaemic risk measures;

identifying an optimal relative time interval for the subject, from among the plurality of relative time intervals associated with the plurality of bins, for injecting the short acting insulin medicament dosage for a prospective meal event using the plurality of first glycaemic risk measures; and communicating the optimal relative time interval to a health care practitioner associated with the subject or directly to the subject.

16. A computer program comprising instructions that, when executed by one or more processors, perform the method of embodiment 15.

17. A computer-readable data carrier having stored thereon the computer program according to embodiment 16.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIGS. 1, 2, 3, 5 and/or described in FIG. 4. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

The invention claimed is:

1. A device for optimizing a timing of a short acting insulin medicament dosage in a prescribed insulin regimen for a subject, wherein the device comprises one or more processors and a memory, the memory comprising:

instructions that, when executed by the one or more processors, perform a method of:

obtaining, in a first stage of a learning phase, a first data set, the first data set comprising a plurality of autonomous glucose measurements of the subject taken over a time course and, for each respective glucose measurement in the plurality of glucose measurements, a corresponding timestamp representing when in the time course the respective glucose measurement was made;

identifying a plurality of meal events in the first data set that occurred during the time course;

obtaining a second data set that specifies, for each respective meal event in the plurality of meal events, when a short acting insulin medicament dosage was injected by the subject relative to an occurrence of the respective meal event;

segmenting the first data set into a plurality of segments, wherein each segment comprises glucose measurements that are associated with a period related to a meal event of the plurality of meal events; binning the plurality of segments of the first data set into a plurality of bins using the second data set, wherein each segment, associated with a respective meal event, is binned by determining when the short acting insulin medicament dosage was injected by the subject relative to the occurrence of the respective meal event, wherein each respective bin in the plurality of bins is associated with a relative time interval in a plurality of relative time intervals, each respective relative time interval in the plurality of relative time intervals defines a different time range for when the short acting insulin medicament dosage was injected by the subject relative to the occurrence of the meal event, and each respective bin is assigned glucose measurements in the plurality of glucose measurements that are associated with one or more periods within the time course in which the subject took the short acting insulin medicament dosage within the relative time interval associated with the respective bin;

in a second stage of the learning phase, providing, to the subject, a request for the subject to vary an injection time in which the short acting insulin medicament dosage is injected by the subject, receiving a further plurality of autonomous glucose measurements of the subject after providing the request, and updating the first data set and the second data set based on receipt of the further plurality of autonomous glucose measurements;

terminating the learning phase based on at least one of detection of an adverse autonomous glucose measurement or based on executing a number of stages of the learning phase equal to a predetermined limit;

following the learning phase, determining a first glycaemic risk measure for each respective bin in the plurality of bins using the autonomous glucose measurements assigned to the respective bin, thereby forming a plurality of first glycaemic risk measures;

identifying an optimal relative time interval for the subject, from among the plurality of relative time intervals associated with the plurality of bins, for injecting the short acting insulin medicament dosage for a prospective meal event using the plurality of first glycaemic risk measures; and communicating the optimal relative time interval to a health care practitioner associated with the subject or directly to the subject.

2. The device of claim 1, wherein the first glycaemic risk measure is calculated for a respective bin in the plurality of bins as:

(i) a percentage of the time the glucose level of the subject is above a first target range across the glucose measurements assigned to the respective bin, (ii) a percentage of the time the glucose level of the subject is below the first target range across the glucose measurements assigned to the respective bin, (iii) a percentage of the time the glucose level of the subject is outside the first target range in the glucose measurement assigned to the respective bin, (iv) a measure of spread of the glucose measurements assigned to the respective bin, (v) a minimum glucose level in the glucose measurements assigned to the respective bin, or (vi) a maximum glucose level in the glucose measurements assigned to the respective bin.

3. The device of claim 1, wherein the first glycaemic risk measure is calculated for a respective bin in the plurality of bins as:

(i) a range of the glucose measurements assigned to the respective bin, (ii) an interquartile range of glucose measurements assigned to the respective bin, (iii) a variance of the glucose measurements assigned to the respective bin, (iv) an average squared difference of the glucose measurements assigned to the respective bin from the mean ($\mu$) of the glucose measurements assigned to the respective bin ($\sigma^2$) computed as:

$$\sigma^2 = \frac{\sum_{i}^{P}(m_i - \mu)^2}{P}$$

wherein, $m_i$ is the $i^{th}$ glucose measurement assigned to the respective bin, and P is a number of glucose measurements assigned to the respective bin, or (v) a standard deviation of the glucose measurements assigned to the respective bin computed as $\sqrt{\sigma^2}$.

4. The device of claim 1, wherein the identifying the plurality of meal events is performed using the plurality of autonomous glucose measurements and the corresponding timestamps in the first data set.

5. The device of claim 4, wherein the identifying the plurality of meal events is performed by computing:

(i) a first model comprising a backward difference estimate of glucose rate of change using the plurality of autonomous glucose measurements, (ii) a second model comprising a backward difference estimate of glucose rate of change based on Kalman filtered estimates of glucose using the plurality of autonomous glucose measurements, (iii) a third model comprising a Kalman filtered estimate of glucose and Kalman filtered estimate of rate of change (ROC) of glucose based on the plurality of autonomous glucose measurements, or (iv) a fourth model comprising a Kalman filtered estimate of rate of change of ROC of glucose based on the plurality of autonomous glucose measurements.

6. The device of claim 5, wherein the first model, the second model, the third model and the fourth model are each computed using the plurality of autonomous glucose measurements and each respective meal event in the plurality of meal events is identified at an instance where at least three of the four models indicates a meal event.

7. The device of claim 4, wherein the identifying the plurality of meal events that occur during the time course further comprises receiving a plurality of feed-forward events, wherein each respective feed-forward event in the plurality of feed-forward events represents an instance where the subject has indicated they are having or are about to have a meal, and the plurality of meal events are verified against the plurality of feed-forward events by removing any respective meal event in the plurality of meal events that fails to temporally match a feed-forward event in the plurality of feed-forward events.

8. The device of claim 1, wherein the identifying the plurality of meal events that occur during the time course comprises receiving a plurality of feed-forward events, wherein each respective feed-forward event in the plurality of feed-forward events represents an instance where the subject has indicated they are having or are about to have a meal.

9. The device of claim 1, wherein
the time course comprises a plurality of epochs, each epoch corresponding to a relative time interval in the plurality of relative time intervals;
the second data set specifies the relative time interval in the plurality of relative time intervals for each epoch in the plurality of epochs; and wherein the method further comprises:
sharing the second data set with the subject prior to the time course to enable the subject to inject the short acting insulin medicament dosage at times specified by the second data set relative to respective meal events during the time course, and wherein
the segmenting the first data set comprises assigning, for each respective epoch in the plurality of epochs, all glucose measurements in the respective epoch to the corresponding bin in the plurality of bins specified for the respective epoch by the second data set; and
the determining the first glycaemic risk measure of a respective bin in the plurality of bin collectively uses autonomous glucose measurements assigned to the respective bin.

10. The device of claim 9, wherein each epoch in the plurality of epochs is one week or less, five days or less, three days or less, two days or less, one day or less, or 12 hours or less.

11. The device of claim 1, wherein the method further comprises:
obtaining a third data set from an insulin pen used by the subject to apply the prescribed insulin regimen, the third data set comprising a plurality of insulin medicament records over the time course, each insulin medicament record in the plurality of medicament records comprising:
(i) a respective insulin medicament injection event representing an insulin medicament injection of the short acting insulin medicament dosage into the subject using the insulin pen, and
(ii) a corresponding electronic timestamp that is automatically generated by the insulin pen upon occurrence of the respective insulin medicament injection event, and wherein
the obtaining the second data set comprises temporally matching respective meal events in the plurality of meal events to respective insulin medicament records thereby determining an actual time difference for when the short acting insulin medicament dosage was injected by the subject for each respective meal event relative to the respective meal event,
the segmenting the first data set comprises:
associating, for each respective meal event in the plurality of meal events, a bin in the plurality of bins with the respective meal event using the second data set, wherein the associating matches (i) the actual time difference and (ii) a corresponding relative time interval in the plurality of relative time intervals, and
assigning, for each respective meal event in the plurality of meal events, autonomous glucose measurements in the plurality of autonomous glucose measurements that occur within a time window that ranges from a first predetermined period of time before the respective meal event to a second predetermined period of time after the respective meal event, to the associated bin, and wherein the segmenting associates more than one meal event from the plurality of meal events to each bin in the plurality of bins, and
the determining the first glycaemic risk measure of a respective bin in the plurality of bins collectively uses autonomous glucose measurements assigned to the respective bin.

12. The device of claim 1, wherein the method further comprises:
obtaining a third data set from an insulin pen used by the subject to apply the prescribed insulin regimen, the third data set comprising a plurality of insulin medicament records over the time course, each insulin medicament record in the plurality of medicament records comprising:
(i) a respective insulin medicament injection event representing an insulin medicament injection of the short acting insulin medicament dosage into the subject using the insulin pen, and
(ii) a corresponding insulin event timestamp that is automatically generated by the insulin pen upon occurrence of the respective insulin medicament injection event, and wherein
the obtaining the second data set comprises temporally matching respective meal events in the plurality of meal events to respective insulin medicament records thereby determining an actual time difference for when the short acting insulin medicament dosage was injected by the subject for each respective meal event,
the identifying the plurality of meal events further comprises applying a first characterization to each meal event in the plurality of meal events, wherein the first characterization is one of insulin regimen adherent and insulin regimen nonadherent, wherein a respective meal event is deemed insulin regimen adherent when one or more insulin medicament records in the plurality of insulin medicament records has an insulin event timestamp that is within a predetermined amount of time of the respective meal event, and
a respective meal event is deemed insulin regimen nonadherent when no medicament record in the plurality of medicament records has an insulin event timestamp that is within the predetermined amount of time of the respective meal event,
the segmenting the first data set comprises:
determining, for each respective meal event in the plurality of meal events that is deemed insulin regimen adherent, which bin in the plurality of bins is associated with the respective meal event using the second data set by a procedure comprising:
matching when a short acting insulin medicament dosage was injected by the subject relative to the respective meal event to a corresponding relative time interval in the plurality of relative time intervals, and
assigning, for each respective meal event in the plurality of meal events, autonomous glucose measurements in the plurality of autonomous glucose measurements that occur within a time window that ranges from a first predetermined period of time before the respective meal event to a second predetermined period of time after the respective meal event, to the associated bin, and wherein the segmenting associates more than one meal event from the plurality of meal events to each bin in the plurality of bins, and the determining the first glycaemic risk measure of a respective bin in the plurality of bins collectively uses autonomous glucose measurements assigned to the respective bin.

13. The device of claim 1, wherein successive measurements in the plurality of autonomous glucose measurements are autonomously taken from the subject at an interval rate of 5 minutes or less, 3 minutes or less, or 1 minute or less.

14. The device of claim 1, the method further comprising:
determining a respective second glycaemic risk measure for each respective bin in the plurality of bins using the autonomous glucose measurements in the respective bin, thereby forming a plurality of second glycaemic risk measures, wherein the second respective glycaemic risk measure is other than the first glycaemic measure and is calculated for a respective bin in the plurality of bins as:
(i) a percentage of the time the glucose level of the subject is above a first target range across the glucose measurements assigned to the respective bin,
(ii) a percentage of the time the glucose level of the subject is below the first target range across the glucose measurements assigned to the respective bin,
(iii) a percentage of the time the glucose level of the subject is outside the first target range in the glucose measurement assigned to the respective bin,
(iv) a measure of spread of the glucose measurements assigned to the respective bin,
(v) a minimum glucose level in the glucose measurements assigned to the respective bin, or
(vi) a maximum glucose level in the glucose measurements assigned to the respective bin; and wherein identifying the optimal relative time interval for the subject, from among the plurality of relative time intervals associated with the plurality of bins, for injecting the short acting insulin medicament dosage for a prospective meal event uses the plurality of first glycaemic risk measures and the plurality of second glycaemic risk measures.

15. A method for optimizing a timing of a short acting insulin medicament dosage in a prescribed insulin regimen for a subject, the method comprising:
at a computer comprising one or more processors and a memory:
obtaining, in a first stage of a learning phase, a first data set, the first data set comprising a plurality of autonomous glucose measurements of the subject taken over a time course and, for each respective glucose measurement in the plurality of glucose measurements, a corresponding timestamp representing when in the time course the respective glucose measurement was made;
identifying a plurality of meal events in the first data set that occurred during the time course;
obtaining a second data set that specifies, for each respective meal event in the plurality of meal events, when a short acting insulin medicament dosage was injected by the subject relative to an occurrence of the respective meal event;
segmenting the first data set into a plurality of segments, wherein each segment comprises glucose measurements that are associated with a period related to a meal event of the plurality of meal events;
binning the plurality of segments of the first data set into a plurality of bins using the second data set, wherein each segment, associated with a respective meal event, is binned by determining when the short acting insulin medicament dosage was injected by the subject relative to the occurrence of the respective meal event, wherein each respective bin in the plurality of bins is associated with a relative time interval in a plurality of relative time intervals,
each respective relative time interval in the plurality of relative time intervals defines a different time range for when a short acting insulin medicament dosage was injected by the subject relative to a meal event, and
each respective bin is assigned glucose measurements in the plurality of glucose measurements that are associated with one or more periods within the time course that are related to a meal event, in which the subject took the short acting insulin medicament dosage within the relative time interval associated with the respective bin;
in a second stage of the learning phase, providing, to the subject, a request for the subject to vary an injection time in which the short acting insulin medicament dosage is injected by the subject, receiving a further plurality of autonomous glucose measurements of the subject after providing the request, and updating the first data set and the second data set based on receipt of the further plurality of autonomous glucose measurements;
terminating the learning phase based on at least one of detection of an adverse autonomous glucose measurement or based on executing a number of stages of the learning phase equal to a predetermined limit;
following the learning phase, determining a first glycaemic risk measure for each respective bin in the plurality of bins using the autonomous glucose measurements assigned to the respective bin, thereby forming a plurality of first glycaemic risk measures;
identifying an optimal relative time interval for the subject, from among the plurality of relative time intervals associated with the plurality of bins, for injecting the short acting insulin medicament dosage for a prospective meal event using the plurality of first glycaemic risk measures; and
communicating the optimal relative time interval to a health care practitioner associated with the subject or directly to the subject.

16. A non-transitory computer-readable data carrier having stored thereon a computer program comprising instructions that, when executed by a computer having one or more processors and a memory, perform the method of claim 15.

* * * * *

UNITED STATES PATENT AND TRADEMARK OFFICE
CERTIFICATE OF CORRECTION

| | | |
|---|---|---|
| PATENT NO. | : 11,631,486 B2 | Page 1 of 1 |
| APPLICATION NO. | : 16/323551 | |
| DATED | : April 18, 2023 | |
| INVENTOR(S) | : Aradottir et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1069 days.

Signed and Sealed this
First Day of July, 2025

Coke Morgan Stewart
*Acting Director of the United States Patent and Trademark Office*